(12) United States Patent
Muchowski et al.

(10) Patent No.: US 7,994,338 B2
(45) Date of Patent: Aug. 9, 2011

(54) SMALL MOLECULE INHIBITORS OF KYNURENINE-3-MONOOXYGENASE

(75) Inventors: Paul J. Muchowski, Sunnyvale, CA (US); Joseph M. Muchowski, Westbank (CA); Robert Schwarcz, Baltimore, MD (US); Paolo Guidetti, Baltimore, MD (US)

(73) Assignees: The J. David Gladstone Institutes, San Francisco, CA (US), A Testamentary Trust Established Under The Will Of J. David Gladstone; University Of Maryland, Baltimore, Baltimore, MD (US)

( * ) Notice: Subject to any disclaimer, the term of this patent is extended or adjusted under 35 U.S.C. 154(b) by 734 days.

(21) Appl. No.: 11/840,138

(22) Filed: Aug. 16, 2007

(65) Prior Publication Data
US 2008/0070905 A1    Mar. 20, 2008

Related U.S. Application Data

(60) Provisional application No. 60/838,446, filed on Aug. 16, 2006, provisional application No. 60/951,099, filed on Jul. 20, 2007.

(51) Int. Cl.
*A61K 31/427* (2006.01)
*C07D 277/44* (2006.01)
*C07D 417/06* (2006.01)

(52) U.S. Cl. .................. 548/197; 514/227.8; 514/236.8; 514/254.04; 514/326; 514/370; 544/60; 544/133; 544/367; 546/209

(58) Field of Classification Search .................... 548/197
See application file for complete search history.

(56) References Cited

U.S. PATENT DOCUMENTS

| | | | |
|---|---|---|---|
| 2,921,066 A | | 1/1960 | Worffel et al. |
| 3,010,872 A | | 11/1961 | Worffel et al. |
| 4,107,288 A | | 8/1978 | Oppenheim et al. |
| 5,145,684 A | | 9/1992 | Liversidge et al. |
| 5,856,347 A | * | 1/1999 | Hashiguchi et al. .......... 514/370 |
| 5,877,193 A | | 3/1999 | Cesura et al. |
| 5,958,910 A | | 9/1999 | Cesura et al. |
| 6,191,170 B1 | | 2/2001 | Medina |
| 6,207,709 B1 | | 3/2001 | Varasi et al. |
| 6,583,161 B1 | | 6/2003 | Medina |
| 6,645,909 B2 | * | 11/2003 | Fujita et al. .................... 503/201 |
| 7,183,276 B2 | * | 2/2007 | Sakai et al. ................ 514/228.2 |
| 2005/0085518 A1 | | 4/2005 | Dai et al. |
| 2006/0052456 A1 | | 3/2006 | Autier et al. |
| 2006/0142358 A1 | | 6/2006 | Autier et al. |
| 2008/0070937 A1 | | 3/2008 | Muchowski et al. |

FOREIGN PATENT DOCUMENTS

| | | |
|---|---|---|
| DE | 1121052 | 4/1962 |
| DE | 1249869 B | 9/1967 |
| EP | 0610653 A1 | 8/1994 |
| EP | 0819681 A2 | 1/1998 |
| EP | 0 790 057 | 6/2002 |
| GB | 905369 | 9/1962 |
| JP | 2003/292485 A * | 10/2003 |
| WO | WO 90/09787 A1 | 9/1990 |
| WO | WO 93/05014 | 3/1993 |
| WO | WO 99/28306 | 6/1999 |
| WO | WO 99/28309 | 6/1999 |
| WO | WO-03/072554 A1 * | 9/2003 |
| WO | WO 2005/79790 | 9/2005 |
| WO | WO 2005/103022 | 11/2005 |

OTHER PUBLICATIONS

Chemical Abstracts Registry No. 894531-35-2, indexed in the file Registry on STN Jul. 19, 2006.*
Chemical Abstracts Registry No. 402767-36-6, indexed in the file Registry on STN Mar. 25, 2002.*
An English translation of JP 2003-292485, Oct. 15, 2003.*
Ingle, D.B. et al. "Synthesis of 2-sulfanilamidothiazole derivatives and their antibacterial activity". Database CA [Online] Chemical Abstracts Service, Columbus, Ohio, US; XP002549764 retrieved from STN, Database accession No. 1979:38829.
Joshi, K.C. et al. "Organic Pesticides. Part X. Preparation of Some 2-Amino-4-aryl-5-alkylthiazoles and Related Compounds, *N*-Substituted Aminothiazoles and their Mercurials, and 2-*p*-Fluorophenylimino-4-thiazolidone and its Condensation Products" Journal of the Indian Chemical Society, The Indian Chemical Society, Calcutta, IN, vol. 39, No. 2, Jan. 1, 1962, pp. 121-128, XP000571711.

(Continued)

*Primary Examiner* — Laura L. Stockton
(74) *Attorney, Agent, or Firm* — Foley & Lardner LLP

(57) ABSTRACT

The present invention relates to compounds of formula Ia or Ib below and their tautomers and/or pharmaceutically acceptable salts and compositions and methods of uses thereof.

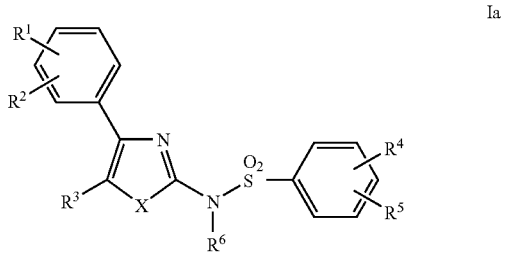

Ia

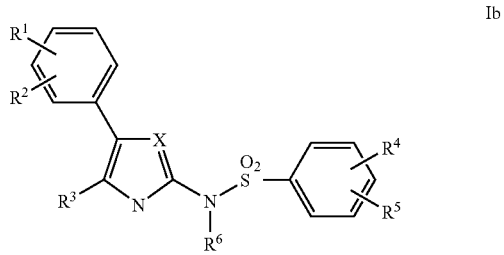

Ib

18 Claims, 13 Drawing Sheets

OTHER PUBLICATIONS

Khan, R.H. et al. "Synthesis of Fluoroarylthiazoles and Related Compounds as Possible Fungicides" Agricultural and Biological Chemistry, Japan Soc. for Bioscience, Biotechnology and Agrochem, Tokyo, JP, vol. 40, No. 6, Jan. 1, 1976, pp. 1129-1135, XP001026659.

Richter, A. et al. "The kynurenine 3-hydroxylase inhibitor Ro 61-8048 improves dystonia in a genetic model of paroxysmal dyskinesia." *European Journal of Pharmacology*, 478 (2003) 47-52.

Rover, et al., J. Med. Chem. 1997, 40, 4378-4385.

R. Schwarcz and R. Pellicciari, The Journal of Pharmacology and Experimental Therapeutics, 2002, vol. 303, No. 1, pp. 1-10.

Bell, F. "Investigations in the Diphenyl Series. Part IX. Further Experiments with Sulphonamides" Journal of the Chemical Society, Chemical Society, Letchworth; GB LNKD-DOI:10.1039/JR9300001071, Jan. 1, 1930, pp. 1071-1077, XP009018773 ISSN: 0368-1769.

Bouchain, G. et al. "Development of Potential Antitumor Agents. Synthesis and Biological Evaluation of a New Set of Sulfonamide Derivates as Histone Deacetylase Inhibitors" Journal of Medicinal Chemistry, American Chemical Society, Washington, US LNKD-DOI:10.1021/JM020377A, vol. 46, Jan. 1, 2003, pp. 820-830, XP002278212. ISSN: 0022-2623.

Bouchain, G. et al. "Novel hydroxamate and anilide derivatives as potent histone deacetylase inhibitors: Synthesis and antiproliferative evaluation" Current Medicinal Chemistry, Bentham Science Publishers BV, BE LNKD-DOI:10.2174/0929867033456585, vol. 10, No. 22, Jan. 1, 2003, pp. 2359-2372, XP002480700, ISSN: 0929-8673.

Case, F. H. "Nitration of certain halo biphenyls. IV. Nitro derivatives of 3-bromobiphenyl" Journal of the American Chemical Society, Coden: JACSAT; ISSN: 0002-7863, vol. 67, 1945, pp. 116-121, XP002590239.

Dhanoa, D.S., et al. "Serine Proteases-Directed Small Molecule Probe Libraries" Medicinal Chemistry Research, Birkhaeuser, Boston, US, vol. 8, No. 4/05, Jan. 1, 1998, pp. 187-205, XP009016618, ISSN: 1054-2523.

El-Hewehi, Zaki. et al. "Sulfonic acid derivatives. III. Preparation, composition, and insecticide activity of sulfonamides" Journal Fuer Praktische Chemie (LEIPZIG), 34(5-6), 218-42 Coden: JPCEAO; ISSN: 0021-8383, 1966, XP009135712.

Erickson et al., A Radiometric Assay for Kynurenine 3-Hydroxylase Based on the Release of 3H2O During Hydroxylation of L-[3,5-3H]-Kynurenine, Anal. Biochem. 1992, 205, 257-262.

Finn, P.W. et al. "Novel Sulfonamide Derivatives as Histone Deacetylase" Helvetica Chimica Acta, Verlag Helvetica Chimica Acta, Basel, CH LNKD-DOI:10.1002/HLCA.200590129, vol. 88, Jul. 1, 2005, pp. 1630-1657, XP002367316. ISSN: 0018-019X.

Raju, B. et al. "Solid Phase Synthesis of Sulfonamides Using a Carbamate Linker" Tetrahedron Letters, Elsevier, Amsterdam, NL LNKD-DOI:10.1016/S0040-4039(97)00652-7, vol. 38, No. 19, May 12, 1997, pp. 3373-3376, XP004061429, ISSN: 0040-4039.

Somaglino, J. C. "Sulfonamides" Database CA [Online] Chemical Abstracts Service, Columbus, Ohio, US; 1941, XP002590240.

* cited by examiner

Plasma Metabolites

Brain Metabolites

Plasma Metabolites

A proportional hazards model of survival shows that the JM6 drug significantly increases survival time ($p < 0.003$).

SMALL MOLECULE INHIBITORS OF KYNURENINE-3-MONOOXYGENASE

CROSS-REFERENCE TO RELATED APPLICATION

This application claims benefit under 35 U.S.C. §119 (e) of U.S. Provisional Application Ser. No. 60/838,446, filed Aug. 16, 2006, and U.S. Provisional Application Ser. No. 60/951,099, filed Jul. 20, 2007, which is hereby incorporated by reference in its entirety.

FIELD OF THE INVENTION

This invention relates generally to benzenesulfonamide compounds and their use as inhibitors of kynurenine-3-monooxygenase.

BACKGROUND OF THE INVENTION

Tryptophan is metabolized in mammals via the kynurenine pathway to yield three neuroactive substances, 3-hydroxykynurenine, kynurenic acid and quinolinic acid. Kynurenic acid has neuroprotective activities in vivo while 3-hydroxykynurenine and quinolinic acid are neurotoxic. Studies have shown that 3-hydroxykynurenine and quinolinic acid are causative or contribute to delayed neurological damages and are associated with a variety of human diseases including neurodegenerative disorders and psychiatric diseases. Pharmacological intervention aimed at blocking 3-hydroxykynurenine and quinolinic acid synthesis and/or increasing kynurenic acid formation have been attempted in treatment of neurological diseases and their peripheral indications, such as diabetes.

Kynurenine-3-monooxygenase (KMO) is an enzyme in the tryptophan degradation pathway that catalyzes the conversion of kynurenine into 3-hydroxykynurenine which is a precursor of the neurotoxin quinolinic acid. Therefore, compounds which act as inhibitors of KMO are of particular interest since they block the metabolism toward quinolinic acid and at the same time, increase the formation of neuroprotective metabolite kynurenic acid.

Inhibitors of KMO have been known in the art. For example, U.S. Pat. No. 5,877,193 describes N-(4-arylthiazol-2-yl)-sulfonamide derivatives for treating neurodegenerative disorders resulting from an activation of the immune system.

There remains a need for compounds that are effective inhibitors of KMO and can be used in treating neurodegenerative disorders. Compounds that inhibit KMO and can thus be used to treat and prevent KMO-associated disorders including neurodegenerative disorders are provided herein.

SUMMARY OF THE INVENTION

This invention is directed to novel compounds, pharmaceutical compositions and methods of using the compounds to inhibit KMO. This invention is also directed to novel intermediates used in the preparation of such compounds.

In one aspect, there are provided compounds of formula Ia or Ib:

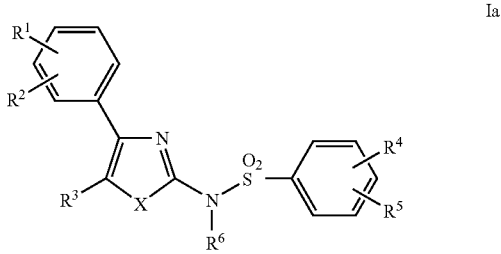

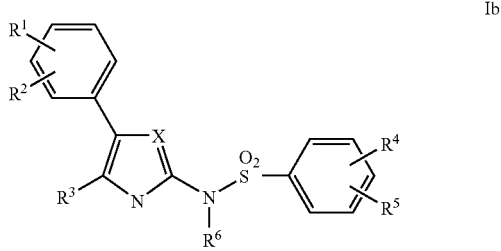

wherein:

X is selected from the group consisting of O, S, and $NR^7$ wherein $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, substituted alkyl, alkoxy, substituted alkoxy, amino, substituted amino, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, amino sulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl; and $R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^3$ or $R^6$ can be hydrogen and with the further proviso that when $R^3$ is hydrogen then $R^6$ is not alkyl.

The invention also provides pharmaceutical compositions comprising one or more compounds of Formula I(a) and/or I(b) and a pharmaceutically acceptable excipient.

In one of its method aspects, this invention is directed to a method for inhibiting activity of kynurenine-3-monooxygenase activity which method comprises contacting cells (including neurons/microglia/invading macrophages) with an effective amount of one or more compound of Formula Ia or Ib:

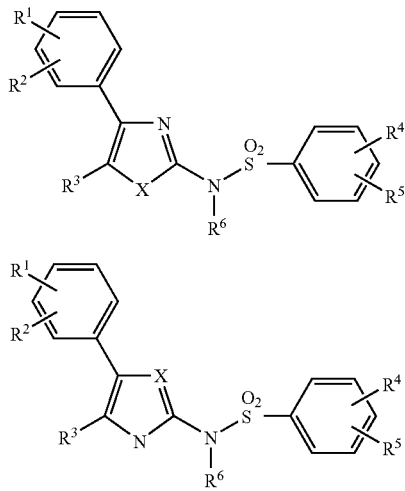

wherein:
X is selected from the group consisting of O, S, and $NR^7$ where $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl; and $R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^3$ or $R^6$ can be hydrogen and with the further proviso that when $R^3$ is hydrogen then $R^6$ is not alkyl.

In another of its method aspects, this invention is directed to a method for treating a disease mediated at least in part by kynurenine-3-monooxygenase which method comprises administering to a patient an effective amount of one or more compounds of Formula I(a) and/or I(b) or a pharmaceutical composition comprising a pharmaceutically acceptable excipient and one or more compound of Formula Ia or Ib:

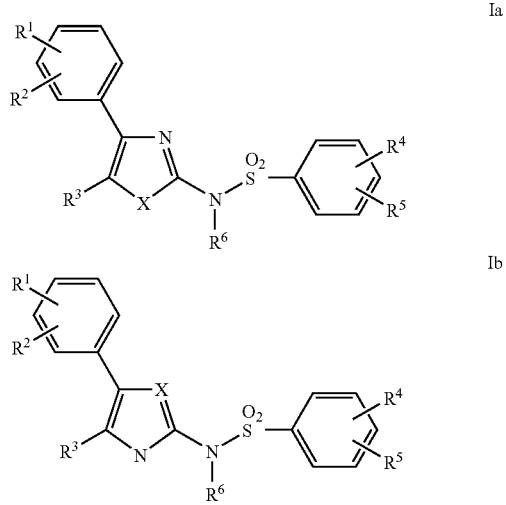

wherein:
X is selected from the group consisting of O, S, and $NR^7$ where $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl; and $R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^3$ or $R^6$ can be hydrogen and with the further proviso that when $R^3$ is hydrogen then $R^6$ is not alkyl.

Diseases mediated at least in part by kynurenine-3-monooxygenase include those selected from the group consisting of Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiatewithdrawal symptoms, feeding behaviour, schizophrenia, chronic anxiety, depressive disorders, disorders of the developing or aged brain, diseases of addiction, diabetes, and complications thereof. The compounds of this invention may also influence synaptogenesis after brain injury. The compounds also may influence memory.

In another of its method aspects, this invention is directed to an article of manufacture for use to inhibit kynurenine-3-monooxygenase for treating a disease mediated at least in part by kynurenine-3-monooxygenase comprising a composition comprising a compound of the Formula Ia or Ib as provided herein. The diseases mediated at least in part by kynurenine-3-monooxygenase are as provided herein. In one embodiment, the article of manufacture further comprises a label with instructions for using the composition to treat a disease mediated at least in part by kynurenine-3-monooxygenase.

BRIEF DESCRIPTION OF THE DRAWINGS

This invention will be further described with reference being made to the accompanying drawings.

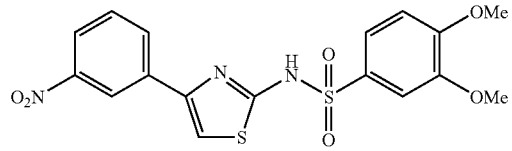

Figure 13:
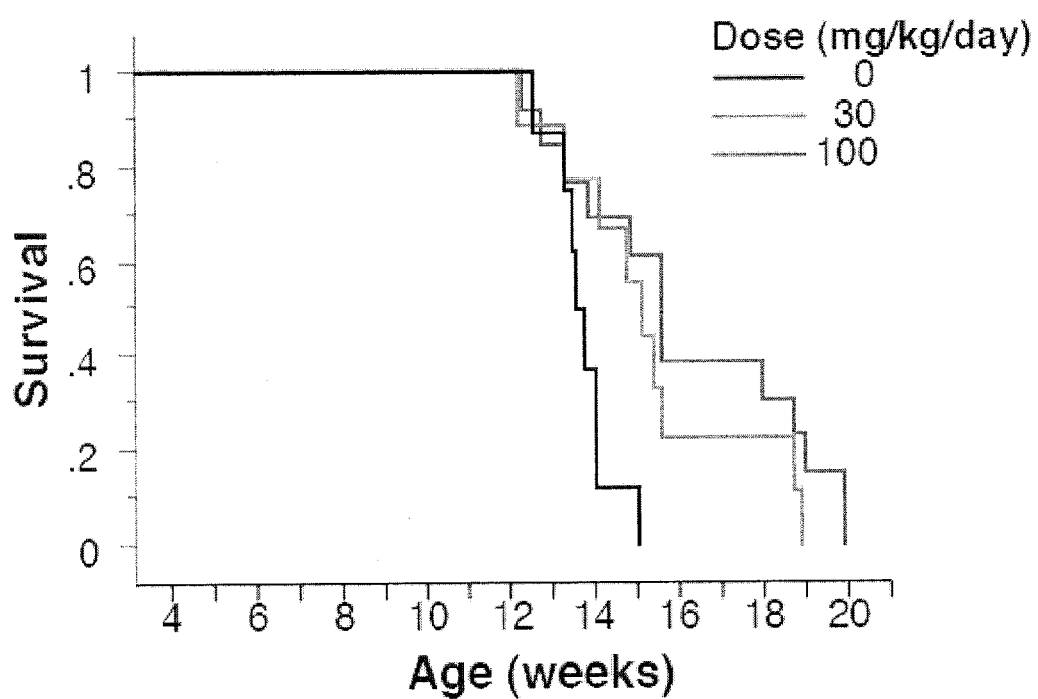

FIG. 13 shows the effect of the compound M (JM6 in FIG. 13) on survival in a mouse model of Huntington's disease. The structure of the compound M is

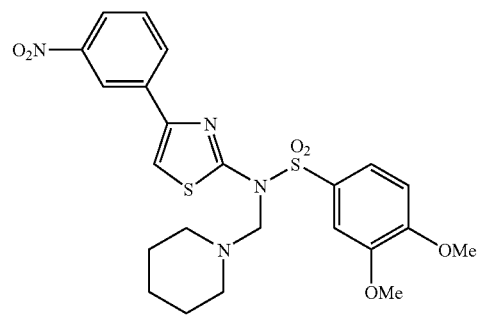

DETAILED DESCRIPTION OF THE INVENTION

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

1. Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2C$≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

Preferred substituted alkyl groups included halogenated alkyl groups and particularly halogenated methyl groups such as trifluoromethyl, difluoromethyl, fluoromethyl and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluoromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}C(O)$alkyl, —$NR^{30}C(O)$substituted alkyl, —$NR^{30}C(O)$cycloalkyl, —$NR^{30}C(O)$substituted cycloalkyl, —N $R^{30}C(O)$alkenyl, —$NR^{30}C(O)$substituted alkenyl, —$NR^{30}C(O)$alkynyl, —$NR^{30}C(O)$substituted alkynyl, —$NR^{30}C(O)$aryl, —$NR^{30}C(O)$substituted aryl, —$NR^{30}C(O)$heteroaryl, —$NR^{30}C(O)$substituted heteroaryl, —$NR^{30}C(O)$heterocyclic, and —$NR^{30}C(O)$substituted heterocyclic wherein $R^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)

O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —$C(O)NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —$C(S)NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}C(O)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —$NR^{30}C(S)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—$C(O)NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —$SO_2NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—$SO_2NR^{33}R^{34}$ where $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —$NR^{30}$—$SO_2NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but non-aromatic cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Sulfinyl" refers to the divalent group —SO—.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cylcoalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluoromethyl, fluoromethyl and the like.

"Sulfonyloxy" or "substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

2. Compounds of the Invention

This invention is directed to compounds, compositions and methods of using the compounds as inhibitors of kynurenine-3-monooxygenase (KMO) and inhibit the KMO activities in the brain.

In one aspect, the present invention provides compounds of Formula Ia or Ib:

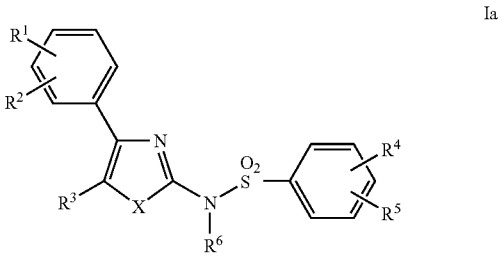

Ia

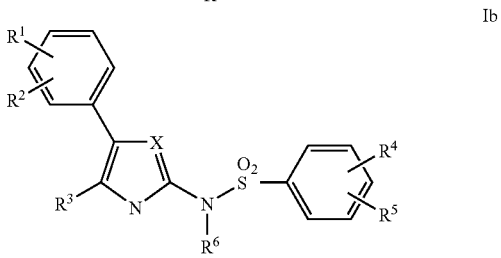

Ib wherein:

X is selected from the group consisting of O, S, and $NR^7$ where $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, substituted alkyl, alkoxy, substituted alkoxy, amino, substituted amino, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl;

$R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^3$ or $R^6$ can be hydrogen and with the further proviso that when $R^3$ is hydrogen then $R^6$ is not alkyl.

In certain embodiments, X is O.
In certain embodiments, X is S.
In certain embodiments, X is NH.
In certain embodiments, X is $NR^7$.
In certain embodiments, $R^1$ and $R^2$ independently are hydrogen or nitro.
In certain embodiments, $R^4$ and $R^5$ independently are hydrogen or alkoxy.
In certain embodiments, $R^3$ is hydrogen or substituted alkyl.
In certain embodiments, $R^6$ is hydrogen, alkyl, substituted alkyl, carboxyl, or carboxyl ester.

In another aspect, the present invention provides compounds of Formula Ia or Ib:

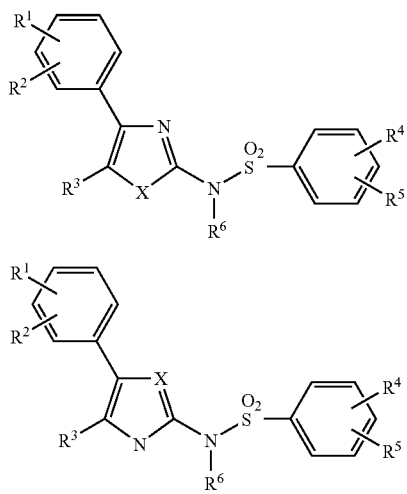

wherein:
X is selected from the group consisting of O, S, and $NR^7$ where $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of substituted alkyl, alkoxy, substituted alkoxy, amino, substituted amino, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof.

In certain embodiments of the aforementioned aspect of the invention, X is O. In certain embodiments, X is S. In certain embodiments, X is NH. In certain embodiments, X is $NR^7$.

In certain embodiments, $R^1$ and $R^2$ independently are hydrogen or nitro.

In certain embodiments, $R^4$ and $R^5$ independently are hydrogen or alkoxy.

In certain embodiments, $R^3$ is substituted alkyl.

In certain embodiments, $R^6$ is hydrogen, alkyl, substituted alkyl, carboxyl, or carboxyl ester.

In certain embodiments, the invention relates to compounds of Formula II:

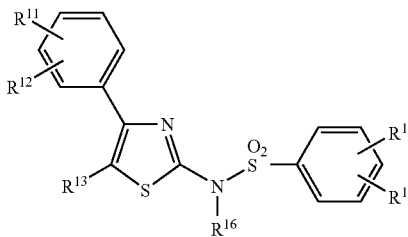

wherein:
$R^{11}$ and $R^{12}$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^{11}$ and $R^{12}$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^{13}$ is selected from the group consisting of hydrogen, substituted alkyl, alkoxy, substituted alkoxy, amino, substituted amino, aryl, substituted aryl, heteroaryl, and substituted heteroaryl;

$R^{14}$ and $R^{15}$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^{14}$ and $R^{15}$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl; and $R^{16}$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^{13}$ or $R^{16}$ can be hydrogen and with the further proviso that when $R^{13}$ is hydrogen then $R^{16}$ is not alkyl.

In certain embodiments, at least one of $R^{11}$ and $R^{12}$ is hydrogen, nitro, trifluoromethyl, cyano, or halo. In particular embodiments, at least one of $R^{11}$ and $R^{12}$ is hydrogen or nitro.

In certain embodiments, at least one of $R^{14}$ and $R^{15}$ is hydrogen or alkoxy. In particular embodiments, at least one of $R^{14}$ and $R^{15}$ is hydrogen or methoxy.

In certain embodiments, $R^{13}$ is hydrogen or substituted alkyl. In particular embodiments, $R^{13}$ is selected from the group consisting of hydrogen, hydroxymethyl, dimethylaminomethyl, pyrrolidin-1-ylmethyl, piperidin-1-ylmethyl, morpholinomethyl, (4-methylpiperazin-1-yl)methyl, (diethylamino)methyl, (methylpropylamino)methyl, thiomorpholinomethyl, and bis(hydroxyethyl)amino)methyl.

In certain embodiments, $R^{16}$ is hydrogen, alkyl, substituted alkyl, carboxyl, or carboxyl ester. In particular embodiments, $R^{16}$ is selected from the group consisting of hydrogen, methyl, (dimethylamino)methyl, pyrrolidin-1-ylmethyl, piperidin-1-ylmethyl, morpholinomethyl, thiomorpholinomethyl, (4-methylpiperazin-1-yl)methyl, (diethylamino)methyl, (methyl(propyl)amino)methyl, (bis(2-hydroxyethyl)amino)methyl, (ethylcarboxylate)methyl, ethylcarboxylate, and methylcarboxylate.

In certain embodiments, the invention relates to compounds of Formula II wherein:

at least one of $R^{11}$ and $R^{12}$ is hydrogen or nitro;

$R^{13}$ is hydrogen or substituted alkyl;

at least one of $R^{14}$ and $R^{15}$ is hydrogen or alkoxy; and $R^{16}$ is hydrogen, alkyl, substituted alkyl, carboxyl, or carboxyl ester;

or a tautomer and/or a pharmaceutically acceptable salt thereof.

In particular embodiments, the invention relates to compounds of Formula II wherein $R^{11}$ is hydrogen and $R^{12}$ is nitro;

$R^{13}$ is selected from the group consisting of hydrogen, hydroxymethyl, dimethylaminomethyl, pyrrolidin-1-ylmethyl, piperidin-1-ylmethyl, morpholinomethyl, (4-methylpiperazin-1-yl)methyl, (diethylamino)methyl, (methylpropylamino)methyl, thiomorpholinomethyl, and bis(hydroxyethyl)amino)methyl;

$R^{14}$ and $R^{15}$ are methoxy; and $R^{16}$ selected from the group consisting of hydrogen methyl, (dimethylamino)methyl, pyrrolidin-1-ylmethyl, piperidin-1-ylmethyl, morpholinomethyl, thiomorpholinomethyl, (4-methylpiperazin-1-yl)methyl, (diethylamino)methyl, (methyl(propyl)amino)methyl, (bis(2-hydroxyethyl)amino)methyl, (ethylcarboxylate)methyl, ethylcarboxylate, and methylcarboxylate;

or a tautomer and/or a pharmaceutically acceptable salt thereof.

In certain embodiments, the invention relates to compounds of Formula II:

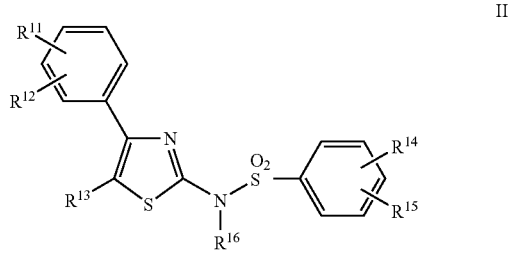

wherein:

$R^{11}$ and $R^{12}$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^{11}$ and $R^{12}$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^{13}$ is selected from the group consisting of substituted alkyl, alkoxy, substituted alkoxy, amino, substituted amino, heteroaryl, and substituted heteroaryl;

$R^{14}$ and $R^{15}$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, or $R^{14}$ and $R^{15}$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl; and $R^{16}$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof.

In certain embodiments of the aforementioned aspect of the invention, at least one of $R^{11}$ and $R^{12}$ is hydrogen, nitro, trifluoromethyl, cyano, or halo. In particular embodiments, at least one of $R^{11}$ and $R^{12}$ is hydrogen or nitro.

In certain embodiments, at least one of $R^{14}$ and $R^{15}$ is hydrogen or alkoxy. In particular embodiments, at least one of $R^{14}$ and $R^{15}$ is hydrogen or methoxy.

In certain embodiments, $R^{13}$ is substituted alkyl. In particular embodiments, $R^{13}$ is selected from the group consisting of hydroxymethyl, dimethylaminomethyl, pyrrolidin-1-ylmethyl, piperidin-1-ylmethyl, morpholinomethyl, (4-methylpiperazin-1-yl)methyl, (diethylamino)methyl, (methylpropylamino)methyl, thiomorpholinomethyl, and bis (hydroxyethyl)amino)methyl.

In certain embodiments, $R^{16}$ is hydrogen, alkyl, substituted alkyl, carboxyl, or carboxyl ester. In particular embodiments, R[16] is selected from the group consisting of hydrogen, methyl, (dimethylamino)methyl, pyrrolidin-1-ylmethyl, piperidin-1-ylmethyl, morpholinomethyl, thiomorpholinomethyl, (4-methylpiperazin-1-yl)methyl, (diethylamino)methyl, (methyl(propyl)amino)methyl, (bis(2-hydroxyethyl)amino)methyl, (ethylcarboxylate)methyl, ethylcarboxylate, and methylcarboxylate.

Compounds of the invention include, but are not limited to,
3,4-dimethoxy-N-[4-(3-nitrophenyl)-5-dimethylaminomethyl-1,3-thiazole-2-yl]benzenesulfonamide;
3,4-dimethoxy-N-[4-(3-nitrophenyl)-5-(pyrrolidin-1-ylmethyl)-1,3-thiazole-2-yl]benzenesulfonamide;
3,4-dimethoxy-N-[4-(3-nitrophenyl)-5-(piperidin-1-ylmethyl)-1,3-thiazole-2-yl]benzenesulfonamide;
3,4-dimethoxy-N-[4-(3-nitrophenyl)-5-morpholinomethyl-1,3-thiazole-2-yl]benzenesulfonamide;
3,4-dimethoxy-N-[4-(3-nitrophenyl)-5-((4-methylpiperazin-1-yl)methyl)-1,3-thiazole-2-yl]benzenesulfonamide;
3,4-dimethoxy-N-[4-(3-nitrophenyl)-5-(diethylamino)methyl-1,3-thiazole-2-yl]benzenesulfonamide;
3,4-dimethoxy-N-[4-(3-nitrophenyl)-5-(methylpropylamino)methyl-1,3-thiazole-2-yl]benzenesulfonamide;
3,4-dimethoxy-N-[4-(3-nitrophenyl)-5-thiomorpholinomethyl-1,3-thiazole-2-yl]benzenesulfonamide;
3,4-dimethoxy-N-[4-(3-nitrophenyl)-5-(bis(hydroxyethyl)amino)methyl)-1,3-thiazole-2-yl]benzenesulfonamide;
3,4-dimethoxy-N-[4-(3-nitrophenyl)-5-(hydroxymethyl)-1,3-thiazole-2-yl]benzenesulfonamide;
3,4-dimethoxy-N-[4-(3-nitrophenyl)thiazol-2-yl]-N-[(dimethylamino)methyl]-benzenesulfonamide;
3,4-dimethoxy-N-[4-(3-nitrophenyl)thiazol-2-yl]-N-(pyrrolidin-1-ylmethyl)benzenesulfonamide;
3,4-dimethoxy-N-[4-(3-nitrophenyl)thiazol-2-yl]-N-(piperidin-1-ylmethyl)benzenesulfonamide;
3,4-dimethoxy-N-[4-(3-nitrophenyl)thiazol-2-yl]-N-(morpholinomethyl)benzenesulfonamide;
3,4-dimethoxy-N-[4-(3-nitrophenyl)thiazol-2-yl]-N-(thiomorpholinomethyl)benzenesulfonamide;
3,4-dimethoxy-N-[4-(3-nitrophenyl)thiazol-2-yl]-N-[(4-methylpiperazin-1-yl)methyl]benzenesulfonamide;
3,4-dimethoxy-N-[4-(3-nitrophenyl)thiazol-2-yl]-N-[(diethylamino)methyl]benzenesulfonamide;
3,4-dimethoxy-N-[4-(3-nitrophenyl)thiazol-2-yl]-N-[(methyl(propyl)amino)methyl]benzenesulfonamide;
3,4-dimethoxy-N-[4-(3-nitrophenyl)thiazol-2-yl]-N-[(bis(2-hydroxyethyl)amino)methyl]benzenesulfonamide;
3,4-dimethoxy-N-[4-(3-nitrophenyl)thiazol-2-yl]-N-(methyl)benzenesulfonamide;
3,4-dimethoxy-N-[4-(3-nitrophenyl)thiazol-2-yl]-N-[(ethylcarboxylate)methyl]benzenesulfonamide;
3,4-dimethoxy-N-[4-(3-nitrophenyl)thiazol-2-yl]-N-(ethylcarboxylate)benzenesulfonamide; and
3,4-dimethoxy-N-[4-(3-nitrophenyl)thiazol-2-yl]-N-(methylcarboxylate)benzenesulfonamide;
or their tautomers and/or a pharmaceutically acceptable salt thereof.

The following Table 1 provides exemplary compounds according to some embodiments of the present invention.

TABLE 1

| Compound Structure | Compound Name |
|---|---|
| 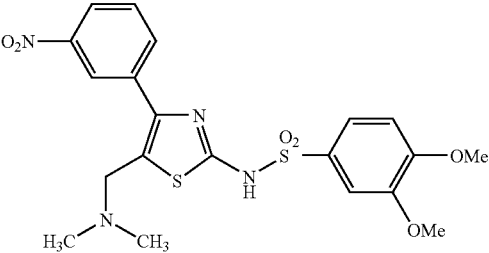 | 3,4-dimethoxy-N-[4-(3-nitrophenyl)-5-dimethylaminomethyl-1,3-thiazole-2-yl]benzenesulfonamide |
| A | |
| 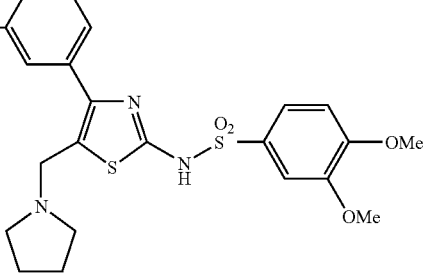 | 3,4-dimethoxy-N-[4-(3-nitrophenyl)-5-(pyrrolidin-1-ylmethyl)-1,3-thiazole-2-yl]benzenesulfonamide |
| B | |

TABLE 1-continued

| Compound Structure | Compound Name |
| --- | --- |
| C | 3,4-dimethoxy-N-[4-(3-nitrophenyl)-5-(piperidin-1-ylmethyl)-1,3-thiazole-2-yl]benzenesulfonamide |
| D | 3,4-dimethoxy-N-[4-(3-nitrophenyl)-5-morpholinomethyl-1,3-thiazole-2-yl]benzenesulfonamide |
| E | 3,4-dimethoxy-N-[4-(3-nitrophenyl)-5-((4-methylpiperazin-1-yl)methyl)-1,3-thiazole-2-yl]benzenesulfonamide |
| F | 3,4-dimethoxy-N-[4-(3-nitrophenyl)-5-(diethylamino)methyl-1,3-thiazole-2-yl]benzenesulfonamide |

TABLE 1-continued

| Compound Structure | Compound Name |
|---|---|
| G | 3,4-dimethoxy-N-[4-(3-nitrophenyl)-5-(methylpropylamino)methyl-1,3-thiazole-2-yl]benzenesulfonamide |
| H | 3,4-dimethoxy-N-[4-(3-nitrophenyl)-5-(N-thiomorpholino)methyl-1,3-thiazole-2-yl]benzenesulfonamide |
| I | 3,4-dimethoxy-N-[4-(3-nitrophenyl)-5-(bis(hydroxyethyl)amino)methyl)-1,3-thiazole-2-yl]benzenesulfonamide |
| J | 3,4-dimethoxy-N-[4-(3-nitrophenyl)-5-(hydroxymethyl)-1,3-thiazole-2-yl]benzenesulfonamide; |

TABLE 1-continued

| Compound Structure | Compound Name |
|---|---|
| 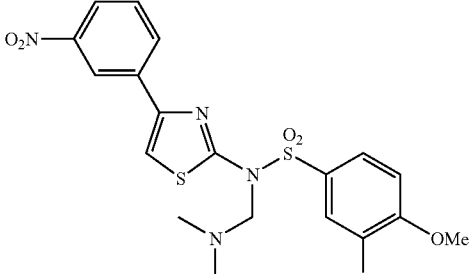 K | 3,4-dimethoxy-N-[4-(3-nitrophenyl)thiazol-2-yl]-N-[(dimethylamino)methyl]-benzenesulfonamide |
| 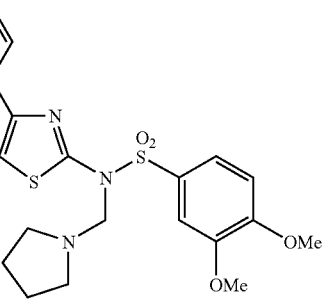 L | 3,4-dimethoxy-N-[4-(3-nitrophenyl)thiazol-2-yl]-N-(pyrrolidin-1-ylmethyl)benzenesulfonamide |
| 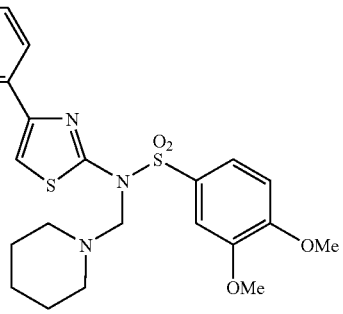 M | 3,4-dimethoxy-N-[4-(3-nitrophenyl)thiazol-2-yl]-N-(piperidin-1-ylmethyl)benzenesulfonamide |
| 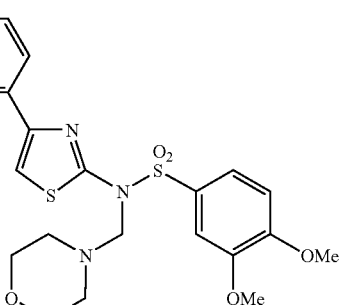 N | 3,4-dimethoxy-N-[4-(3-nitrophenyl)thiazol-2-yl]-N-(morpholinomethyl)benzene-sulfonamide |

TABLE 1-continued

| Compound Structure | Compound Name |
|---|---|
| O | 3,4-dimethoxy-N-[4-(3-nitrophenyl)thiazol-2-yl]-N-(thiomorpholinomethyl)-benzenesulfonamide |
| P | 3,4-dimethoxy-N-[4-(3-nitrophenyl)thiazol-2-yl]-N-[(4-methylpiperazin-1-yl)methyl]benzenesulfonamide |
| Q | 3,4-dimethoxy-N-[4-(3-nitrophenyl)thiazol-2-yl]-N-[(diethylamino)methyl]benzenesulfonamide |
| R | 3,4-dimethoxy-N-[4-(3-nitrophenyl)thiazol-2-yl]-N-[(methyl(propyl)amino)methyl]benzenesulfonamide |

TABLE 1-continued

| Compound Structure | Compound Name |
|---|---|
| S | 3,4-dimethoxy-N-[4-(3-nitrophenyl)thiazol-2-yl]-N-[(bis(2-hydroxyethyl)amino)methyl]benzenesulfonamide |
| T | 3,4-dimethoxy-N-[4-(3-nitrophenyl)thiazol-2-yl]-N-(methyl)benzenesulfonamide |
| U | 3,4-dimethoxy-N-[4-(3-nitrophenyl)thiazol-2-yl]-N-[(ethylcarboxylate)methyl]benzenesulfonamide |
| V | 3,4-dimethoxy-N-[4-(3-nitrophenyl)thiazol-2-yl]-N-(ethylcarboxylate)benzenesulfonamide |

TABLE 1-continued

| Compound Structure | Compound Name |
|---|---|
| 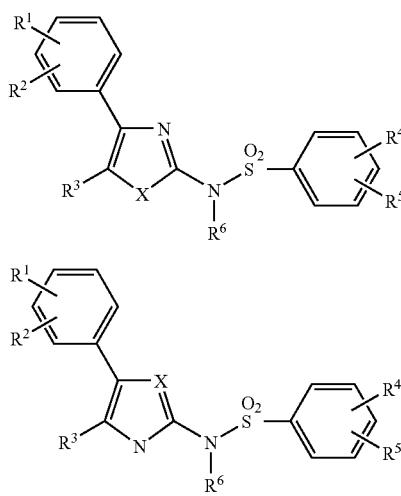<br>W | 3,4-dimethoxy-N-[4-(3-nitrophenyl)thiazol-2-yl]-N-(methylcarboxylate)benzenesulfonamide |

3. Compositions and Methods of the Invention

The compounds represented by formula Ia or Ib or their tautomers and/or pharmaceutically acceptable salts thereof can effectively act as inhibitors of KMO and inhibit the KMO activities in the brain. In one aspect of the invention, the invention provides pharmaceutical compositions comprising one or more compounds of Formula Ia or Ib and a pharmaceutically acceptable excipient. In another aspect of this invention, the invention provides a method for inhibiting activity of kynurenine-3-monooxygenase activity and/or a method for treating a disease mediated at least in part by kynurenine-3-monooxygenase with an effective amount of one or more compound of Formula Ia or Ib as provided herein. The compounds of the invention are useful in inhibiting the activity of kynurenine-3-monooxygenase activity in the CNS as well as in peripheral immune cells. The compounds are also useful for treating peripheral infections or immune dysfunction.

In one of its method aspects, this invention is directed to a method for inhibiting activity of kynurenine-3-monooxygenase activity which method comprises contacting cells (including neurons/microglia/invading macrophages) with an effective amount of one or more compound of Formula Ia or Ib:

Ia

Ib wherein:

X is selected from the group consisting of O, S, and $NR^7$ where $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl; and $R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^3$ or $R^6$ can be hydrogen and with the further proviso that when $R^3$ is hydrogen then $R^6$ is not alkyl.

In another of its method aspects, this invention is directed to a method for treating a disease mediated at least in part by kynurenine-3-monooxygenase which method comprises administering to a patient an effective amount of one or more compounds of Formula I(a) and/or I(b) or a pharmaceutical composition comprising a pharmaceutically acceptable excipient and one or more compound of Formula Ia or Ib:

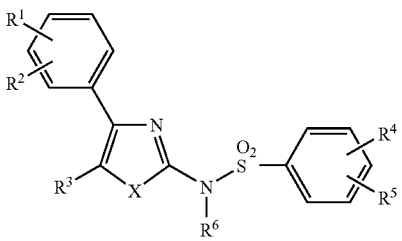

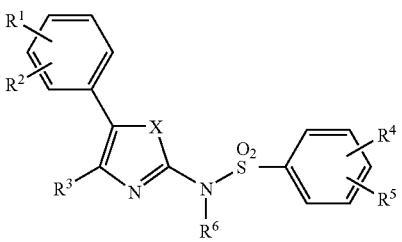

wherein:

X is selected from the group consisting of O, S, and $NR^7$ where $R^7$ is selected from the group consisting of hydrogen, alkyl, substituted alkyl, amino, substituted amino, aryl, substituted aryl, heteroaryl, and substituted heteroaryl;

$R^1$ and $R^2$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^1$ and $R^2$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

$R^3$ is selected from the group consisting of hydrogen, alkyl, substituted alkyl, alkoxy, substituted alkoxy, halo, amino, substituted amino, aryl, substituted aryl, heteroaryl, and substituted heteroaryl;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, or $R^4$ and $R^5$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl; and $R^6$ is selected from the group consisting of hydrogen, alkyl, substituted alkyl, carboxyl, carboxyl ester, aryl, substituted aryl, heteroaryl, and substituted heteroaryl;

or a tautomer and/or a pharmaceutically acceptable salt thereof with a proviso that only one of $R^3$ or $R^6$ can be hydrogen and with the further proviso that when $R^3$ is hydrogen then $R^6$ is not alkyl.

Diseases mediated at least in part by kynurenine-3-monooxygenase include those selected from the group consisting of Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiatewithdrawal symptoms, feeding behaviour, schizophrenia, chronic anxiety, depressive disorders, disorders of the developing or aged brain, diseases of addiction, diabetes, and complications thereof. The compounds of this invention may also influence synaptogenesis after brain injury. The compounds also may influence memory. The diseases of addiction refer to addictive diseases which adversely affect or alter the neuronal function including by way of example, drug addition such as alcoholism, nicotine addiction, illicit drug addiction (e.g., heroine, cocaine, marijuana, etc.).

The compounds of this invention are useful in the diagnosis and treatment of a variety of human diseases including neurodegenerative and neurological disorders, consequences of stroke and/or cerebral ischaemia, hypoxia, multi-infarct dementia, consequences of trauma and damages to the cerebrum or spinal cord, autoimmune disease, and psychiatric illness. For example, the compounds of the present invention are particularly useful in treating neurodegenerative disorders such as Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiatewithdrawal symptoms, feeding behaviour, schizophrenia, chronic anxiety, depressive disorders, disorders of the developing or aged brain, diseases of addiction, all peripheral indications such as diabetes, and complications thereof. The compounds of this invention may also influence synaptogenesis after brain injury. The compounds also may influence memory.

4. General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Synthesis of Compounds of the Invention

In one general embodiment, the method involves reacting an appropriate benzenesulfonyl halide with an appropriate amine.

For example, the compounds of general formula Ia or Ib can be prepared according to Scheme 1:

Scheme 1

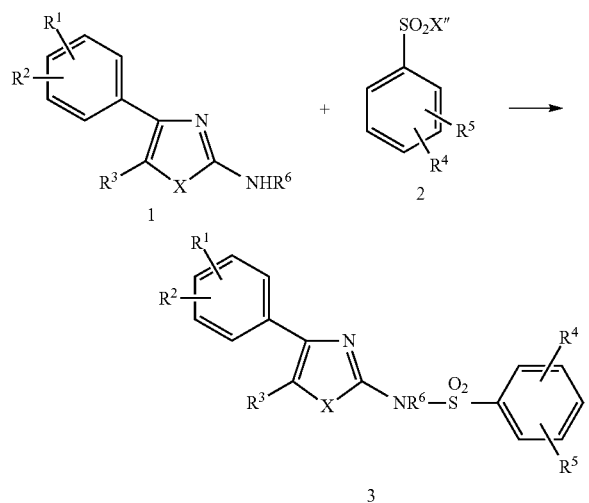

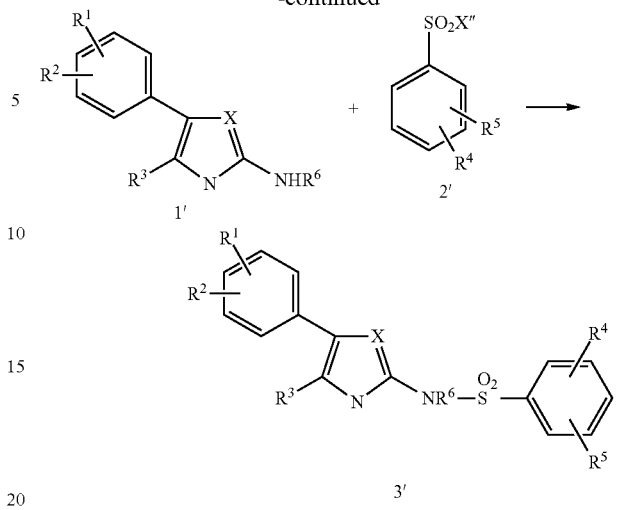

wherein X" represents halogen and $R^1$-$R^6$ and X are as defined herein.

In Scheme 1, compound 1 is combined with an equimolar amount and preferably an excess of compound 2 under coupling conditions to provide for compound 3. Specifically, this reaction is typically conducted by reacting amino compound 1 with at least one equivalent, preferably about 1.1 to about 2 equivalents, of sulfonyl halide (e.g., chloride), compound 2, in an inert diluent such as dichloromethane and the like. Generally, the reaction is conducted at a temperature ranging from about −70° C. to about 40° C. for about 1 to about 24 h. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Alternatively, compound 1 can be reacted with compound 2 in pyridine solution where pyridine acts both as a base and as a solvent. Upon completion of the reaction, the resulting N-sulfonyl compound 3 is recovered by conventional methods including neutralization, extraction, precipitation, chromatography, filtration, and the like.

The sulfonyl halides of compound 2 are either known compounds or compounds that can be prepared from known compounds by conventional synthetic procedures. Such compounds are typically prepared from the corresponding sulfonic acid, i.e., from compounds of the formula Ph($R^4$)($R^5$)SO$_3$H where $R^4$ and $R^5$ are as defined above, using phosphorous trihalide and phosphorous pentahalide. This reaction is generally conducted by contacting the sulfonic acid with about 2 to 5 molar equivalents of phosphorous trihalide and phosphorous pentahalide, either neat or in an inert solvent, such as dichloromethane, at temperature in the range of about 0° C. to about 80° C. for about 1 to about 48 h to afford the sulfonyl halide. Alternatively, the sulfonyl halides can be prepared from the corresponding thiol compound, i.e., from compounds of the formula Ph($R^4$)($R^5$)SH where $R^4$ and $R^5$ are as defined above, by treating the thiol with chlorine (Cl$_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfon, chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl compound 3.

Amino compounds 1 or 1' can be prepared from known compounds or can be prepared in analogy to known methods. For example, the appropriate aryl-substituted amino-thiazole can be prepared according to Scheme 2:

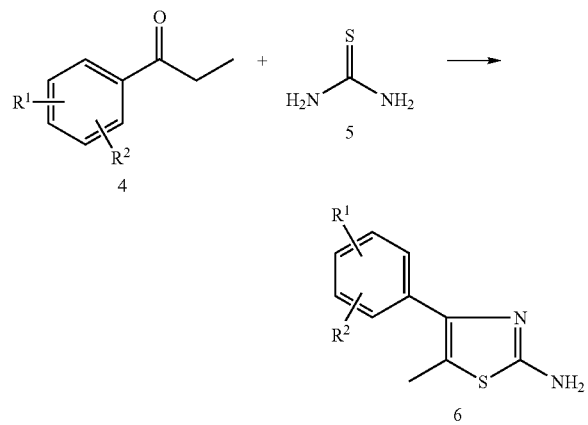

where $R^1$ and $R^2$ are as described herein.

This reaction is typically conducted by adding equimolar amounts of compound 4 and 5 in a polar solvent, such as ethanol or isopropanol, at a temperature ranging from about 40° C. to about 100° C. The product can be recovered by conventional methods such as crystallization.

Other known heteroarylamines can be prepared in a manner similar to the above and are illustrated in the examples below. Alternatively, heteroarylamines can be prepared using methodology well known in the art such as Suzuki coupling of an aromatic or heteroaromatic halide with an aromatic or heteroaromatic boron derivative using techniques well known in the art. Typically, some of such heteroarylamines can be commercially available from vendors such as Aldrich Chemical Company including, for example, 3-amino-5-phenylpyrazole, 2-amino-5-phenyl-1,3,4-thiadiazole, 2-amino-4-(p-tolyl)-thiazole, 2-amino-4-(4-bromophenyl)-thiazole, 2-amino-4-(4-chlorophenyl)-thiazole, and the like.

In addition to the above, compounds of formula Ia or Ib having substitution on the amino group of the sulfonamide can be prepared as a post-synthetic modification of the compounds of formula Ia or Ib with no substitution on the amino group of the sulfonamide. One embodiment is shown below in Scheme 3 for the synthesis of derivatives of 3,4-dimethoxy-N-[4-(3-nitrophenyl)thiazol-2-yl]benzenesulfonamide:

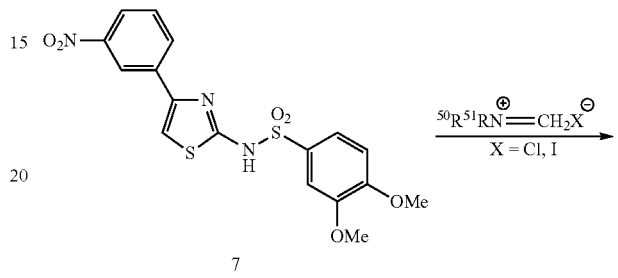

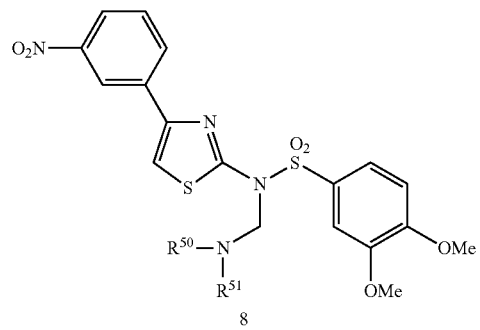

In Scheme 3, the aminomethylene derivative, compound 8, can be prepared using well known Eschenmoser salts or Mannich base salts in polar solvents, such as ethanol, under elevated temperatures.

In another embodiment, derivatives of 3,4-dimethoxy-N-[4-(3-nitrophenyl)thiazol-2-yl]benzenesulfonamide can be prepared by Scheme 4 as follows:

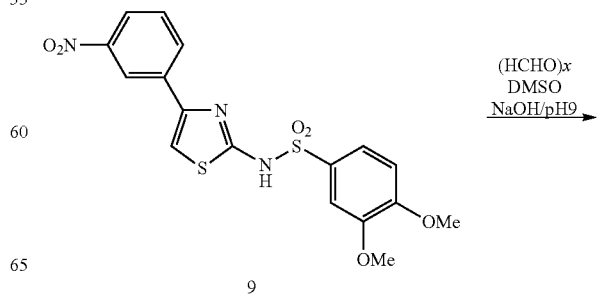

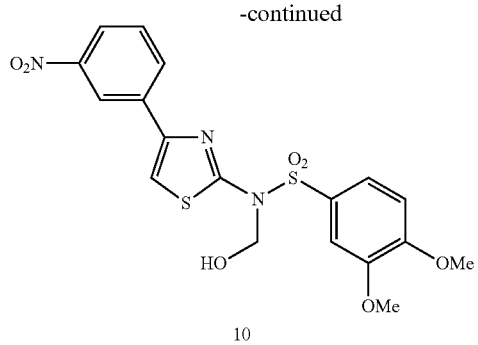

10

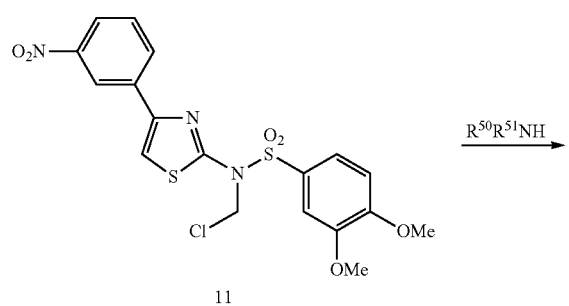

11

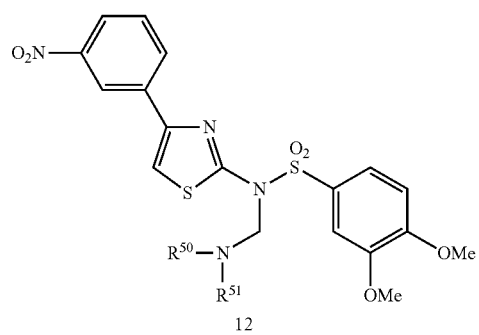

12

Such derivations are contemplated to allow for active metabolites to be formed in the brain rather than in the peripheral circulation and inhibits KMO activity in the brain upon metabolic activation as an irreversible enzyme inhibitor.

5. Use of Compounds of the Invention

The compounds in accordance with the present invention have high activities as inhibitors of kynurenine-3-monooxygenase.

The KMO inhibiting activities of the compounds of the present invention were evaluated using standard methods. See Erickson et al., A Radiometric Assay for Kynurenine 3-Hydroxylase Based on the Release of $^3H_2O$ During Hydroxylation of L-[3,5-$^3$H]-Kynurenine, *Anal. Biochem.* 1992, 205, 257-262, the disclosure of which is hereby incorporated by reference.

Table 2 shows $IC_{50}$ values or percent inhibition for some of the compounds of this invention. The $IC_{50}$ value is the half maximal inhibitory concentration and represents the concentration of an inhibitor that is required for 50% inhibition of an enzyme activity and the percent inhibition measures the amount of enzyme activity inhibited at a given concentration of compound.

TABLE 2

| Compound[#] | % inhibition at 10 µM |
|---|---|
| A | 58 |
| B | 9* |
| C | 24 |
| D | 64 |
| E | 6* |
| F | 74 |
| G | 73 |
| T | 52 |
| U | 81 |
| V | 84 |
| W | 85 |

*Prodrug entity: may not inhibit KMO until metabolized appropriately
[#]The compounds in this table have been identified in Table 1 herein

6. Administration and Pharmaceutical Composition

The present invention provides novel compounds possessing KMO inhibition activity and, accordingly, are useful in treating disorders mediated by (or at least in part by) the presence of 3-hydroxykynurenine and/or quinolinic acid. Such diseases include, for example, Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiatewithdrawal symptoms, feeding behaviour, schizophrenia, chronic anxiety, depressive disorders, disorders of the developing or aged brain, diabetes, and complications thereof.

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, preferably once or twice a day.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

This invention is not limited to any particular composition or pharmaceutical carrier, as such may vary. In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present invention based on the total formulation, with the balance being one or more suitable pharmaceutical excipients. Preferably, the compound is present at a level of about 1-80 wt %. Representative pharmaceutical formulations are described below.

FORMULATION EXAMPLES

The following are representative pharmaceutical formulations containing a compound of formula Ia or Ib.

Formulation Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Formulation Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |

| Ingredient | Amount |
|---|---|
| colorings | 0.5 mg |
| distilled water | q.s. to 100 mL |

Formulation Example 4

Injectable Formulation

The following ingredients are mixed to form an injectable formulation.

| Ingredient | Amount |
|---|---|
| compound of this invention | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| Compound of the invention | 500 mg |
| Witepsol ® H-15 | balance |

The following synthetic and biological examples are offered to illustrate this invention and are not to be construed in any way as limiting the scope of this invention. Unless otherwise stated, all temperatures are in degrees Celsius.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

| | |
|---|---|
| $CaCl_2$ = | calcium chloride |
| bd = | broad doublet |
| bdd = | broad doublet of doublets |
| bm = | broad multiplet |

| | |
|---|---|
| bs = | broad singlet |
| bt = | broad triplet |
| d = | doublet |
| dd = | doublet of doublets |
| DMF = | dimethylformamide |
| DMSO = | dimethyl sulfoxide |
| EtOAc = | ethyl acetate |
| EtOH = | ethanol |
| g = | gram |
| h = | hour/s |
| HCl = | hydrochloric acid |
| HCHO = | formaldehyde |
| HOAc = | acetic acid |
| Hz = | hertz |
| m = | multiplet |
| M = | molar |
| MeOH = | methanol |
| mg = | milligrams |
| mL = | milliliters |
| mmol = | millimols |
| mp = | melting point |
| MS = | mass spectroscopy |
| m/z = | mass to charge ratio |
| NaCl = | sodium chloride |
| $Na_2CO_3$ = | sodium carbonate |
| NMR = | nuclear magnetic resonance |
| NaOH = | sodium hydroxide |
| $Na_2SO_4$ = | sodium sulfate |
| q = | quartet |
| s = | singlet |
| t = | triplet |
| TLC = | thin layer chromatography |
| UV = | ultraviolet |
| wt % = | weight percent |

Example 1

3-Nitro-N-[4-(3,4-dimethoxyphenyl)thiazol-2-yl]benzenesulfonamide

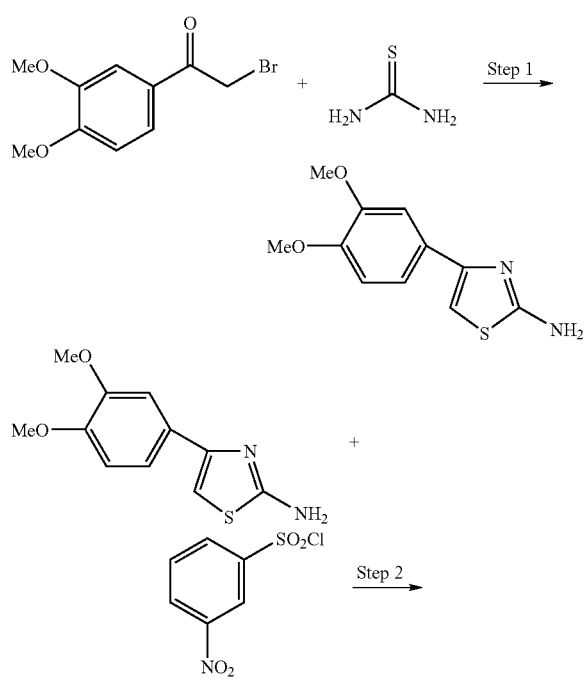

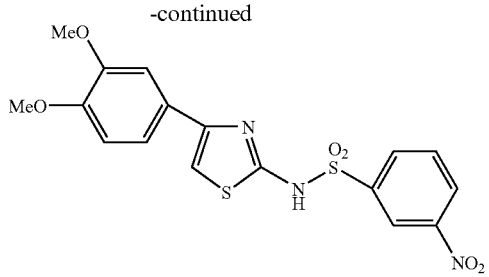

Step 1:

To a solution of thiourea (114 mg, 1.5 mmol) in ethanol (10 mL) was added 2-bromo-1-(3,4-dimethoxyphenyl)ethanone (389 mg, 1.5 mmol). The mixture was stirred and heated to reflux. 5 mL ethanol was added to the mixture during reflux. After 1.5 h at reflex temperature, the mixture was cooled down to room temperature and the solvent was removed in vacuo. The residue was taken up in water and the solution was brought to about pH 9 with 10 wt % $Na_2CO_3$. The mixture was extracted with EtOAc. The extract was washed with saturated NaCl solution, dried over $Na_2SO_4$, and the solvent was removed in vacuo to give a solid (0.352 g) which was crystallized from ethanol to give 245 mg of yellow green needles, mp 191-193° C. A second crop was obtained from the mother liquor, 28 mg, mp 185-189° C.

Another reaction was run on the same scale, i.e., 114 mg (1.5 mmol) of thiourea dissolved in ethanol (10 mL) to which was added 389 mg (1.5 mmol) of 2-bromo-1-(3,4-dimethoxyphenyl)ethanone followed by 5 mL of ethanol. The mixture was heated to reflux. After 1.5 h at reflux, the mixture was cooled down to room temperature, and the solvent was removed in vacuo. The residual solid was taken up in water and made acidic to pH ~2 with 1M HCl. The mixture was washed with EtOAc and the acid phase was made basic with solid $Na_2CO_3$ and extracted with EtOAc. The extract was washed with saturated NaCl solution, dried over $Na_2SO_4$, and the solvent was removed in vacuo. 307 mg of a solid residue was obtained. This was slurried with cold ethanol and the yellow solid was collected and dried in vacuo to give 260 mg of product mp 190-191.5° C. A second crop was obtained from the mother liquor (9 mg, 190-191.5° C.). Total yield was 269 mg (75.5%).

Step 2:

A mixture of 4-(3,4-dimethoxyphenyl)thiazol-2-amine (354 mg, 1.50 mmol) in dry pyridine (2 mL) was stirred and 3-nitrobenzenesulfonyl chloride (367 mg, 1.55 mol) was added. The mixture was stirred at room temperature with protection from moisture by a drying tube filled with $CaCl_2$ for 16 h, then the pyridine was removed in vacuo at 40° C. The residual oil was partitioned between EtOAc and 1M HCl (5 mL). The organic phase was shaken with 5 mL of 1M HCl, then with water. It was dried over $Na_2SO_4$ and evaporated in vacuo to give 485 mg of a foam. The foam was dissolved in 20 mL of 2M NaOH and 20 mL of EtOH to give a red colored solution. This solution was made slightly acidic with concentrated HCl to give a solid material which was taken up in EtOAc, washed with water and evaporated in vacuo to give a red glass (376 mg). The product was taken up again in EtOAc, treated with charcoal, filtered and evaporated in vacuo to give 277 mg of a yellow foam. The yellow foam was taken up in 1:1 ethanol, 1M NaOH (10 mL) and brought to pH 3 with drop wise addition and stirring of 1M HCl. A yellow solid separated from the red colored solution. After stirring to effect granulation the solid was collected by filtration, washed with cold 40:60 EtOH—H$_2$O and dried in vacuo. The yellow powder weighed 256 mg. The product was not crystalline and did not have a distinct melting point.

Example 2

3,4-Dimethoxy-N-[4-(3-nitrophenyl)thiazol-2-yl]benzenesulfonamide

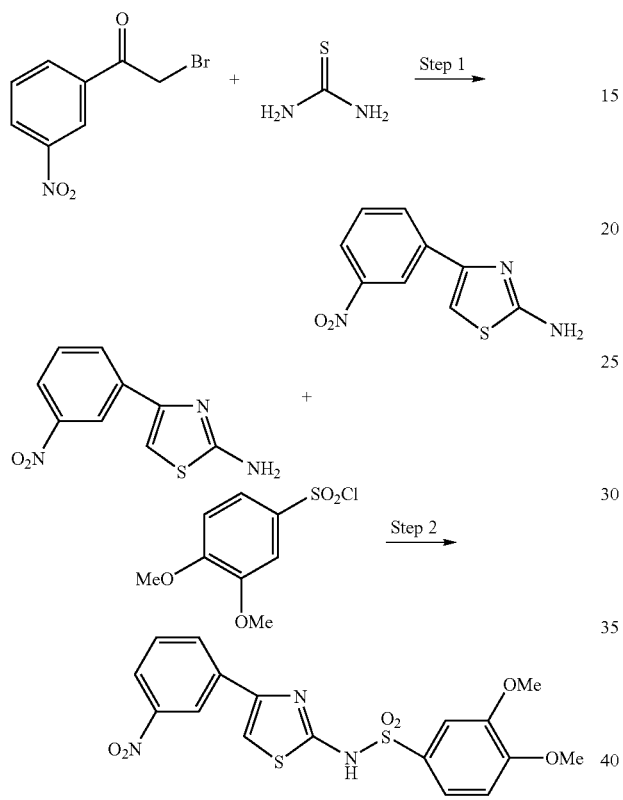

Step 1:

Thiourea (1.523 g, 20 mmol) was dissolved with warming in ethanol (135 mL). After the mixture was cooled down to room temperature, 2-bromo-1-(3-nitrophenyl)ethanone (4.881 g, 20 mmol) was added with vigorous stirring followed by 70 mL of ethanol. The mixture was stirred and heated at reflux temperature for 1.5 h. The solvent was removed in vacuo and the residue was slurried with water to which had been added solid Na$_2$CO$_3$ to bring the pH to ~9. The product was extracted with a large volume of EtOAc, the extract was washed with water, then with saturated NaCl solution. After drying over Na$_2$SO$_4$ the solvent was removed in vacuo to give 4.49 g of a yellow solid which was crystallized from alcohol. First crop yielded 3.609 g, mp 186-187.5° C. A second crop of 0.5739 g, mp 186.5-188.5° C. was obtained from the mother liquor. Total yield of pure material was 4.182 g (94.5%).

Step 2:

4-(3-Nitrophenyl)thiazol-2-amine (1.10 g, 5.0 mmol) was dissolved in dry pyridine (16 mL) and then 3,4-dimethoxybenzene-1-sulfonyl chloride (1.323 g, 5.59 mmol) was added. The reaction mixture was stirred at room temperature for 23 h and then the pyridine was flashed off in vacuo with toluene. The residue was slurried with EtOAc and water. Full solution was achieved and then ice cold 1M NaOH was added. After thorough shaking, the aqueous phase was separated and the organic phase was twice extracted with 1M NaOH and then with water until no yellow color was extracted. The aqueous extract was combined with the NaOH solution and the solution was made slightly acidic with 3M HCl. The product was extracted into EtOAc, then washed successively with H$_2$O and saturated NaCl solution. After drying over Na$_2$SO$_4$, the solvent was removed in vacuo to give a gum which contained HOAc. This was flashed off with toluene. The foam remained slowly solidified and after drying in vacuo, weighed 1.632 g (77.4%) and was greater than 95% pure by TLC. This material was taken up in hot EtOAc, diluted with about one-half the volume of hexane while hot which induced crystallization. The first crop weighed 1.352 g and was pure by TLC, but had no distinct melting point. Yield of pure material (TLC) was 64.2%.

Example 3

3,4-Dimethoxy-N-[4-(3-nitrophenyl)-5-dimethylaminomethyl-1,3-thiazole-2-yl]benzenesulfonamide

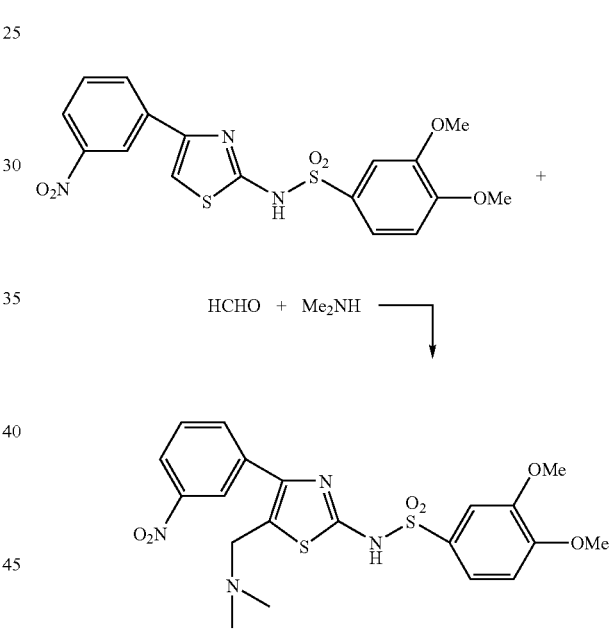

To a stirred solution of 3,4-dimethoxy-N-(4-(3-nitrophenyl)thiazol-2-yl)benzenesulfonamide (0.267 g, 0.68 mmol) in ethanol (10 mL, warming required) was added an aqueous solution of formaldehyde (37%, 0.5 mL, about 0.194 g, 6.5 mmol) followed by the dropwise addition of a solution of dimethylamine in water (60 wt %, 55 mL, about 0.274 g, 6.1 mmol). The addition was slightly exothermic, and the pale yellow solution became yellow-orange in color. After 0.5 h, a pale yellow solid separated from solution. After 19 h, the solid was collected by filtration, it was washed with ethanol, and dried in vacuo to give a pale yellow solid (0.277 g, 86.3% yield), mp 203° C.

$^1$H NMR (DMSO d$_6$) δ 2.26 (s, 6H), 3.59 (bs, 2H), 3.78 (s, 3H), 3.79 (s, 3H), 7.06 (d, J=8.4 Hz, 1H), 7.29 (d, J=2.0 Hz, 1H), 7.41 (dd, J=2.0, 8.4 Hz, 1H), 7.73 (t, 1H), 7.89 (d, J=7.2 Hz, 1H), 7.93 (d, J=7.6 Hz, 1H), 8.38 (bs, 1H), 12.25 (bs, 1H); MS-ESI m/z 479 (MH)$^+$.

Example 4

3,4-Dimethoxy-N-[4-(3-nitrophenyl)-5-(pyrrolidin-1-ylmethyl)-1,3-thiazol-2-yl]benzenesulfonamide Same procedure as Example 3 except for using pyrrolidine as a secondary amine.

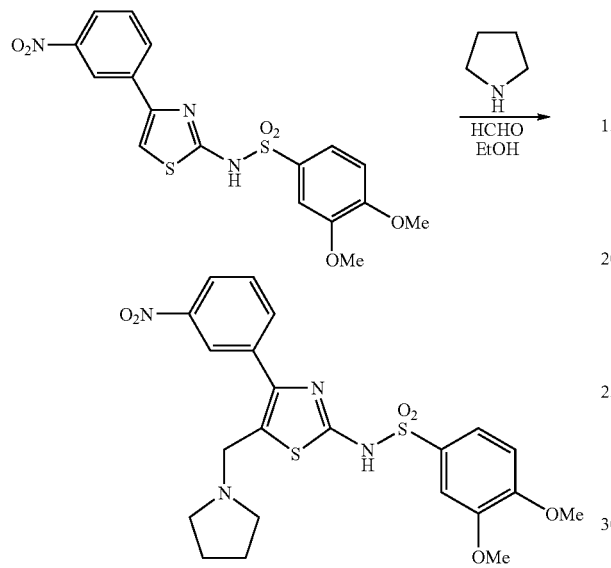

The product was yellow solid in 86% yield with mp 198-200° C.

$^1$H NMR (DMSO d$_6$) δ 1.73 (bs, 4H), 2.67 (bs, 4H), 3.76 (s, 3H), 3.77 (s, 3H), 3.78 (bs, 3H), 7.04 (d, J=8.1 Hz, 1H), 7.27 (d, J=2.1 Hz, 1H), 7.38 (dd, J=2.1, 8.1 Hz, 1H), 7.71 (t, 1H), 7.92 (bd, J=7.8 Hz, 1H), 8.22 (bdd, J=1.6, 8.3 Hz, 1H), 8.39 (s, 1H); MS-ESI m/z 505 (MH)$^+$.

Example 5

3,4-Dimethoxy-N-[4-(3-nitrophenyl)-5-(piperidin-1-ylmethyl)-1,3-thiazol-2-yl]benzenesulfonamide Same procedure as Example 3 except for using piperidine as a secondary amine.

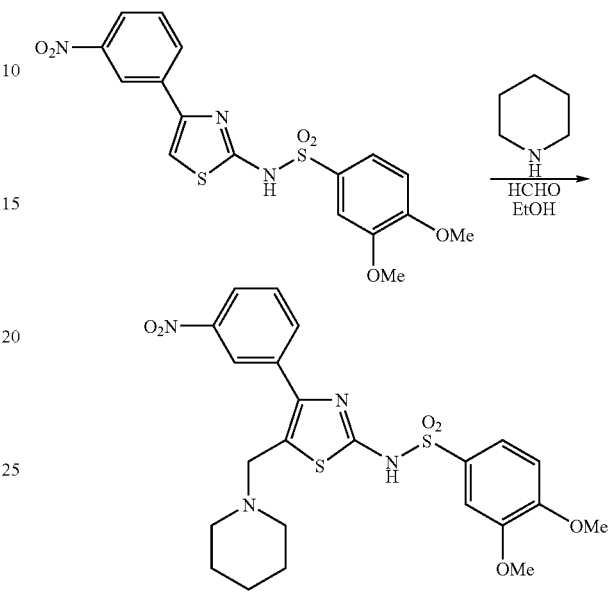

The product was yellow solid in 88% yield with mp 193-194° C.

$^1$H NMR (DMSO d$_6$) δ 1.39 (bs, 2H), 1.52 (bs, 4H), 2.45 (bs, 4H), 3.55 (bs, 2H), 3.79 (s, 3H), 3.83 (s, 3H), 7.07 (d, J=8.4 Hz, 1H), 7.30 (d, J=2.0 Hz, 1H), 7.39 (dd, J=2.0, 8.4 Hz, 1H), 7.74 (t, 1H), 7.93 (d, J=8.0 Hz, 1H), 8.25 (dd, J=1.6, 8.4 Hz, 1H), 8.43 (s, 1H), 12.41 (bs, 1H); MS-ESI m/z 519 (MH)$^+$.

An alternative method for the preparation of 3,4-dimethoxy-N-[4-(3-nitrophenyl)-5-(piperidin-1-ylmethyl)-1,3-thiazol-2-yl]benzenesulfonamide is as described below.

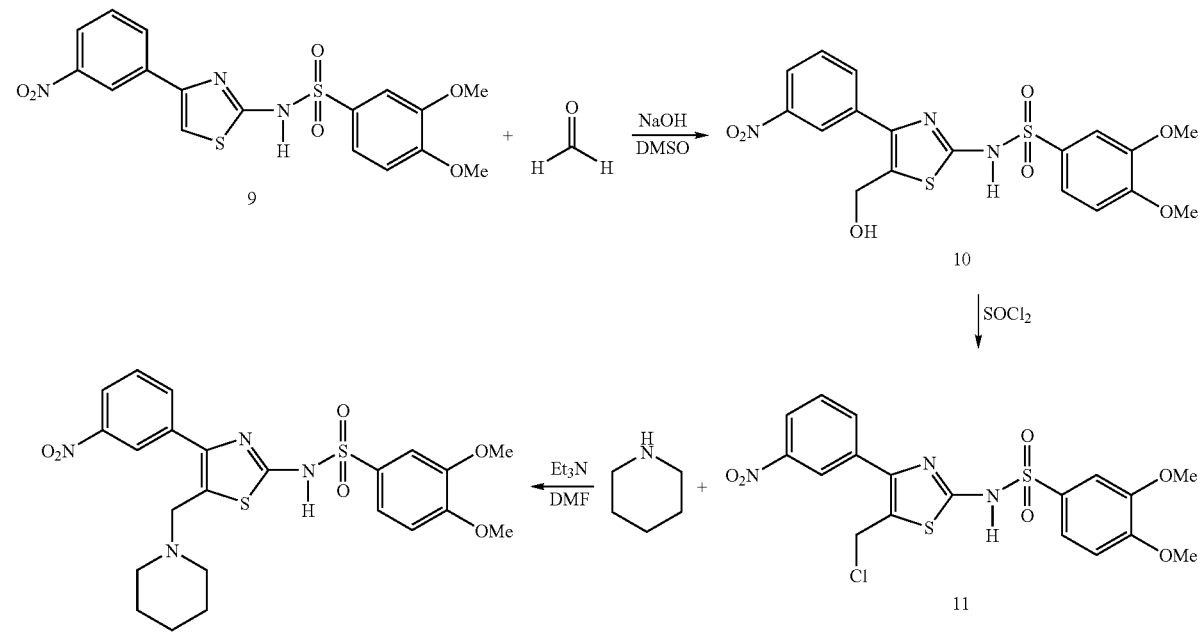

1 M Sodium hydroxide (15 mL) was added to a stirred solution of 3,4-dimethoxy-N-(4-(3-nitrophenyl)thiazol-2-yl)benzenesulfonamide 9 (4.8 g., 11.4 mmol) and paraformaldehyde (0.689 g., 22.8 mmol) in DMSO (10 mL. pH~9) at room temperature. After 24 h, the mixture was partitioned between ethyl acetate and water, the organic phase was dried over anhydrous sodium sulfate, and the solvent was removed in vacuo to give crude compound 10 (5.25 g) which was used as such in the synthesis of compound 11.

Thionyl chloride (10 mL) was added to crude compound 10 (0.500 g) and the mixture was heated at 60° C. for 2 h. The formation of a less polar material was observed by TLC on silica gel. The excess thionyl chloride was removed in vacuo, and the residual crude compound 11 was used in the next step without purification.

Triethylamine (0.161 g, 1.6 mmol) and piperidine (0.8 mmol) were added to a stirred solution of the crude chloride 11 (0.250 g) in dimethyl formamide (5 mL) under a nitrogen atmosphere at room temperature. The reaction mixture was stirred at room temperature overnight and then it was partitioned between ethyl acetate and water. The organic phase was dried over anhydrous sulfate, and the solvent was removed in vacuo. The reaction mixture was subjected to purification by column chromatography on silica gel. The product (0.044 g) was eluted with a dichloromethane-methanol mixture (99:1). The spectral properties of this material were identical to those prepared by method as described supra.

Example 6

3,4-Dimethoxy-N-[4-(3-nitrophenyl)-5-morpholinomethyl-1,3-thiazole-2-yl]benzenesulfonamide The procedure is same as Example 3 except that morpholine is a secondary amine and that after 0.5 h of the reaction, the ethanol was removed in vacuo and the residue was partitioned between water and ethyl acetate. The organic phase was combined with an ethyl acetate extract of the aqueous phase and then it was washed successively with water and saturated sodium chloride solution, dried over anhydrous sodium sulfate, and the solvent was removed in vacuo to give the desired material as solid. The product was yellow solid in 70% yield with mp 143° C.

$^1$H NMR (DMSO d$_6$) δ 2.39 (bs, 4H), 3.48 (bs, 2H), 3.57 (bt, 4H), 3.78 (s, 3H), 3.79 (s, 3H), 7.08 (d, J=8.5 Hz, 1H), 7.28 (d, J=2.1 Hz, 1H), 7.42 (dd, J=2.1, 8.5 Hz, 1H), 7.74 (t, 1H), 7.91 (bd, J=7.8 Hz, 1H), 8.26 (bdd, J=2.2, 7.4 Hz, 1H), 8.45 (t, 1H), 12.92 (bs, 1H); MS-ESI m/z 521 (MH)$^+$.

Example 7

3,4-Dimethoxy-N-[4-(3-nitrophenyl)-5-((4-methylpiperazin-1-yl)methyl)-1,3-thiazole-2-yl]benzenesulfonamide Same procedure as Example 3 except for using N-methylpiperazine as a secondary amine.

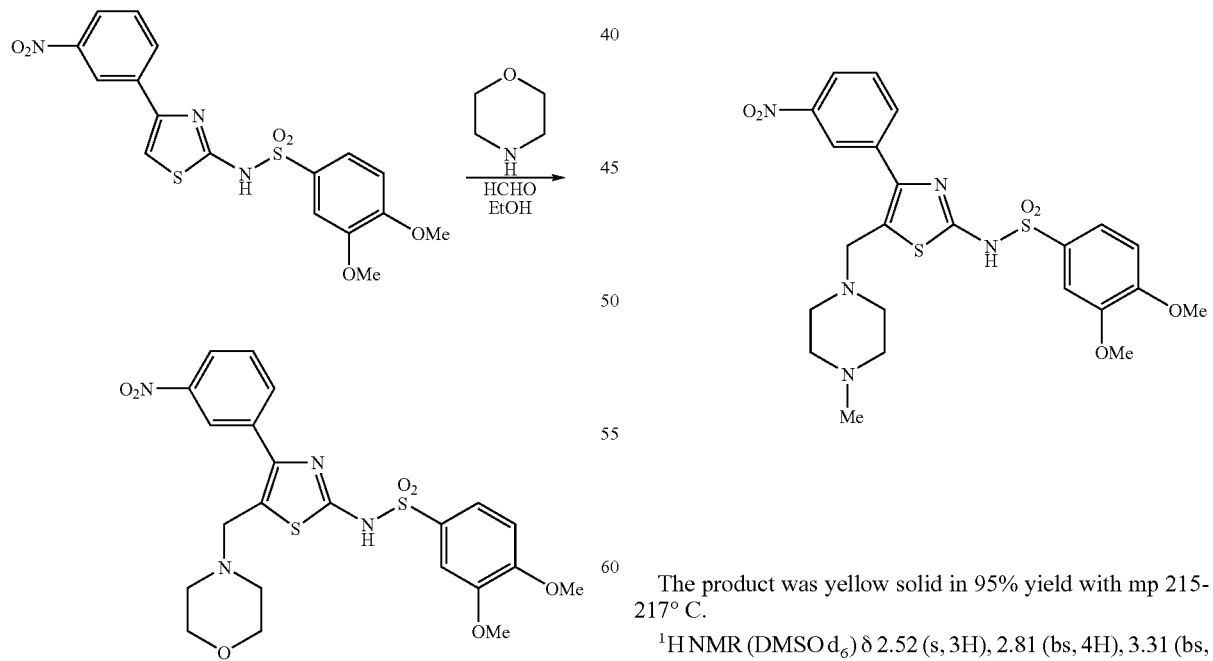

The product was yellow solid in 95% yield with mp 215-217° C.

$^1$H NMR (DMSO d$_6$) δ 2.52 (s, 3H), 2.81 (bs, 4H), 3.31 (bs, 6H), 3.75 (s, 3H), 3.76 (s, 3H), 6.99 (d, J=8.5 Hz, 1H), 7.28 (d, J=1.8 Hz, 1H), 7.36 (dd, J=1.8, 8.5 Hz, 1H), 7.68 (t, 1H), 7.97 (d, J=8.1 Hz, 1H), 8.14 (dd, J=1.5, 8.4 Hz, 1H), 8.56 (bs, 1H); MS-ESI m/z 534 (MH)$^+$.

Example 8

3,4-Dimethoxy-N-[4-(3-nitrophenyl)-5-((diethylamino)methyl)-1,3-thiazole-2-yl]benzenesulfonamide Same procedure as Example 3 except for using diethylamine as a secondary amine.

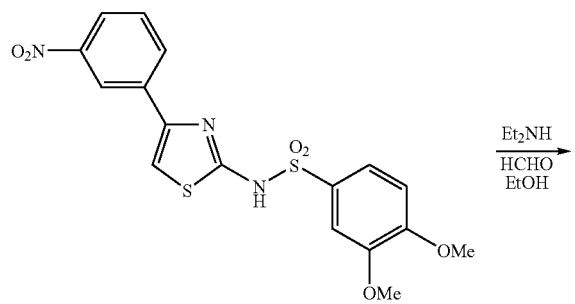

The product was yellow solid in 25% yield with mp 165-168° C.

$^1$H NMR (DMSO d$_6$) δ 0.93 (t, J=7.5 Hz, 6H), 2.33-2.64 (bm, 4H), 3.63 (bs, 2H), 3.77 (s, 3H), 3.79 (s, 3H), 7.05 (d, J=8.4 Hz, 1H), 7.28 (d, J=1.8 Hz, 1H), 7.39 (d, J=8.4 Hz, 1H), 7.73 (t, 1H), 7.91 (d, J=7.8 Hz, 1H), 8.23 (bd, J=7.2 Hz, 1H), 8.34 (s, 1H); MS-ESI m/z 507 (MH)$^+$.

Example 9

3,4-Dimethoxy-N-[4-(3-nitrophenyl)-5-(methylpropylamino)methyl-1,3-thiazole-2-yl]benzenesulfonamide Same procedure as Example 3 except for using N-methylpropylamine as a secondary amine.

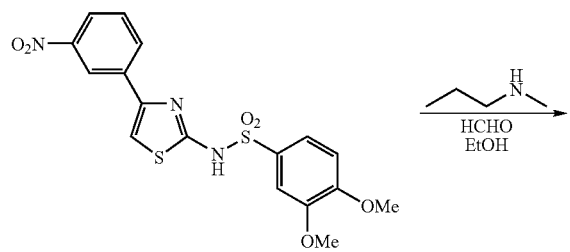

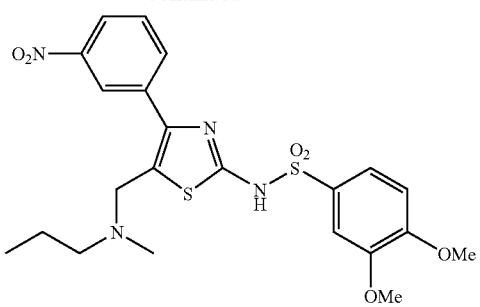

The product was yellow solid in 32% yield with mp 143-145° C.

$^1$H NMR (DMSO d$_6$) δ 0.80 (t, J=7.4 Hz, 3H), 1.46 (m, 2H), 2.18 (bs, 3H), 2.33 (bm, 2H), 3.58 (bs, 2H), 3.77 (s, 3H), 3.79 (s, 3H), 7.06 (d, J=8.7 Hz, 1H), 7.28 (s, 1H), 7.41 (d, J=8.7 Hz, 1H), 7.73 (t, 1H), 7.91 (d, J=8.1 Hz, 1H), 8.23 (d, J=8.4 Hz, 1H), 8.34 (s, 1H); MS-ESI m/z 507 (MH)$^+$.

Example 10

3,4-dimethoxy-N-(4-(3-nitrophenyl)-5-(thiomorpholinomethyl)-1,3-thiazol-2-yl)benzenesulfonamide Same procedure as Example 3 except for using thiomorpholine as a secondary amine.

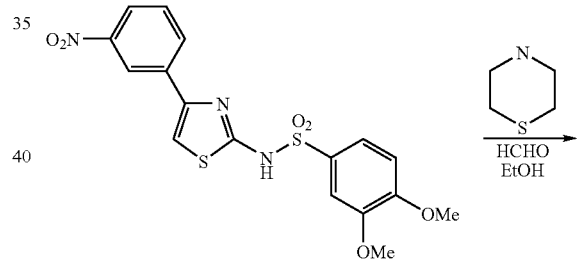

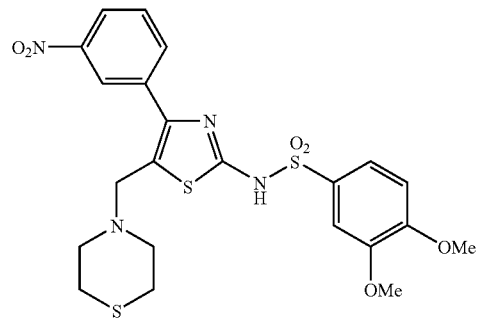

The product was pink solid in 53% yield with mp 136° C.

$^1$H NMR (DMSO d$_6$) δ 2.54-2.71 (m, 8H), 3.47 (s, 2H), 3.76 (s, 3H), 3.77 (s, 3H), 7.03 (d, J=8.2 Hz, 1H), 7.28 (d, J=2.2 Hz, 1H), 7.38 (dd, J=2.2, 8.2 Hz, 1H), 7.70 (t, 1H), 7.95 (d, J=8.1 Hz, 1H), 8.19 (dd, J=1.5, 8.2 Hz, 1H), 8.5 (bs, 1H); MS-ESI m/z 537 (MH)$^+$.

Example 11

3,4-Dimethoxy-N-[4-(3-nitrophenyl)-5-(bis(hydroxyethyl)amino)methyl)-1,3-thiazole-2-yl]benzenesulfonamide Same procedure as Example 3 except for using diethanolamine as a secondary amine.

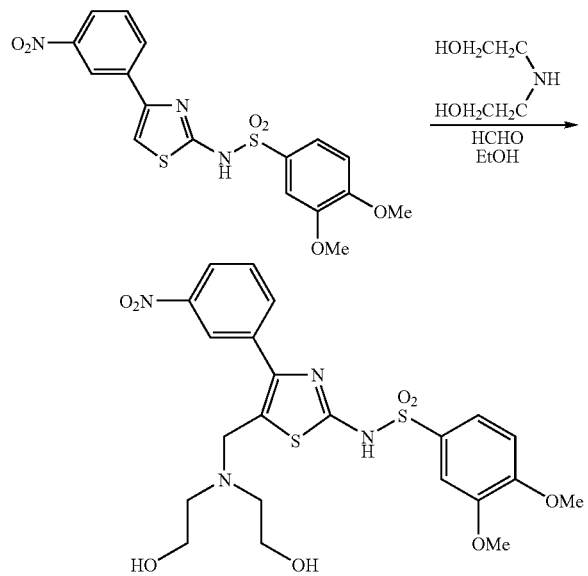

Example 12

3,4-dimethoxy-N-[4-(3-nitrophenyl)thiazol-2-yl]-N-(methyl)benzenesulfonamide

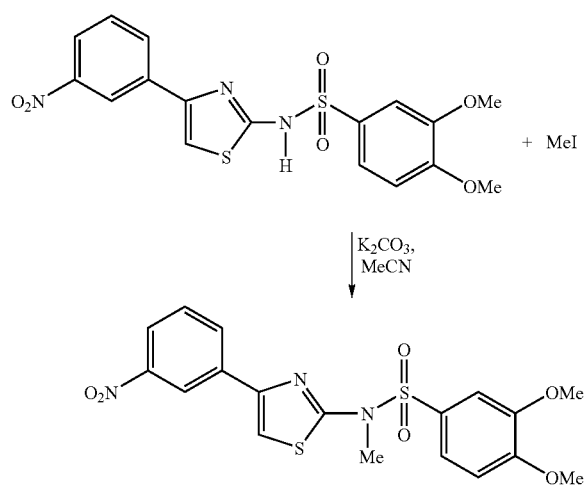

Anhydrous potassium carbonate (0.204 g, 14.8 mmol), and methyl iodide (0.209 g, 14.8 mmol) were added to a stirred solution of 3,4-dimethoxy-N-(4-(3-nitrophenyl)thiazol-2-yl)benzenesulfonamide (0.250 g, 5.94 mmol) in acetonitrile (10 mL) under a nitrogen atmosphere at room temperature. After 2 h, the solvent was removed in vacuo and the residue was partitioned between ethyl acetate and water. The organic phase was dried over anhydrous sodium sulfate, and the solvent was removed in vacuo. The crude reaction mixture was subjected to purification by column chromatography on silica gel. Elution with an ethyl acetate-hexane mixture (20:80) gave 3,4-dimethoxy-N-[4-(3-nitrophenyl)thiazol-2-yl]-N-(methyl)benzenesulfonamide (0.175 g) as a white colored solid.

$^1$H NMR (DMSO $d_6$) δ 3.55 (s, 3H), 3.86 (s, 3H), 3.92 (s, 3H), 7.14 (d, 1H, J=9.4 Hz), 7.34 (d, 1H, J=2.7 Hz), 7.54 (d, 1H, J=7.4 Hz), 7.62 (t, 1H, J=7.4 Hz), 7.73 (s, 1H), 8.16 (d, 1H, J=7.8 Hz), 8.23 (d, 1H, J=7.8 Hz), 8.67 (bs, 1H); MS-ESI m/z 436 (MH)$^+$.

Example 13

3,4-dimethoxy-N-[4-(3-nitrophenyl)thiazol-2-yl]-N-[(ethylcarboxylate)methyl]benzenesulfonamide Same procedure as Example 12 using the commercially available starting materials.

Pale yellow solid. $^1$H NMR (DMSO $d_6$) δ 1.22 (t, 3H, J=8.0 Hz), 3.09 (s, 2H), 3.84 (s, 3H), 3.87 (s, 3H), 4.23 (q, 2H, J=8.0 Hz), 7.14 (d, 1H, J=8.0 Hz), 7.50-7.70 (m, 4H), 8.17 (m, 2H), 8.65 (bs, 1H); MS-ESI m/z 508 (MH)$^+$.

Example 14

3,4-dimethoxy-N-[4-(3-nitrophenyl)thiazol-2-yl]-N-[(ethylcarboxylate)]benzenesulfonamide Same procedure as Example 12 using the commercially available starting materials.

Pale yellow solid. $^1$H NMR (DMSO $d_6$) δ 1.09 (t, 3H, J=7.3 Hz), 3.87 (s, 3H), 3.93 (s, 3H), 4.16 (q, 2H, J=7.3 Hz), 7.29 (d, 1H, J=7.7 Hz), 7.55 (bs, 1H), 7.71 (d, 1H, J=9.3 Hz), 7.81 (d, 1H, J=9.0 Hz), 8.24 (d, 1H, J=8.0 Hz), 8.41 (d, 2H, J=8.3 Hz), 8.69 (m,. 2H); MS-ESI m/e 494 (MH)$^+$.

Example 15

3,4-dimethoxy-N-[4-(3-nitrophenyl)thiazol-2-yl]-N-[(methylcarboxylate)]benzenesulfonamide Same procedure as Example 12 using the commercially available starting materials.

Pale yellow solid. $^1$H NMR (DMSO $d_6$) δ 3.71 (s, 3H), 3.88 (s, 3H), 3.92 (s, 3H), 7.30 (d, 1H, J=7.4 Hz), 7.53 ((bs, 1H), 7.70 (d, 1H, J=7.7 Hz), 7.80 (d, 1H, J=7.4 Hz), 8.26 (d, 1H, J=8.1 Hz), 8.41 (d, 1H, J=8.8 Hz), 8.66 (s, 1H), 8.70 (bs, 1H.

Analogously, following compounds in the Table 3 were also prepared:

TABLE 3

| Example | Compound name |
|---|---|
| 16 | 3,4-dimethoxy-N-[4-(3-nitrophenyl)thiazol-2-yl]-N-[(dimethylamino)methyl]-benzenesulfonamide |
| 17 | 3,4-dimethoxy-N-[4-(3-nitrophenyl)thiazol-2-yl]-N-(pyrrolidin-1-ylmethyl)benzenesulfonamide |
| 18 | 3,4-dimethoxy-N-[4-(3-nitrophenyl)thiazol-2-yl]-N-(piperidin-1-ylmethyl)benzenesulfonamide |
| 19 | 3,4-dimethoxy-N-[4-(3-nitrophenyl)thiazol-2-yl]-N-(morpholinomethyl)benzenesulfonamide |

TABLE 3-continued

| Example | Compound name |
| --- | --- |
| 20 | 3,4-dimethoxy-N-[4-(3-nitrophenyl)thiazol-2-yl]-N(thiomorpholinomethyl)benzenesulfonamide |
| 21 | 3,4-dimethoxy-N-[4-(3-nitrophenyl)thiazol-2-yl]-N-[(4-methylpiperazin-1-yl)methyl]benzenesulfonamide |
| 22 | 3,4-dimethoxy-N-[4-(3-nitrophenyl)thiazol-2-yl]-N-[(diethylamino)methyl]benzenesulfonamide |
| 23 | 3,4-dimethoxy-N-[4-(3-nitrophenyl)thiazol-2-yl]-N-[(methyl(propyl)amino)methyl]benzenesulfonamide |
| 24 | 3,4-dimethoxy-N-[4-(3-nitrophenyl)thiazol-2-yl]-N-[(bis(2-hydroxyethyl)amino)methyl]benzenesulfonamide |

Example 25

Radiolabel Assay Methodology to Measure KMO Activity In Vivo

The graphs shown in FIGS. 1-11 are the results from radiolabel experiments to follow $^3$H-KYN metabolism in vivo. At time zero, mice were treated with vehicle or 100 mg/kg of compounds. After 2 h, mice were injected in the striatum with $^3$H-KYN. After a further 2 h, mice were sacrificed, the brains were removed, and radioactive and non-radioactive KP metabolite levels were analyzed. Data are mean ±SEM values, in percentages of recovered radioactivity of four control and four treated animals. The recovery of injected radioactivity was substantially and significantly decreased for 3-HK and QUIN in most animals treated with A10 vs. vehicle control. *P<0.05 vs. control animals by Student's t-test.

Figure 1:
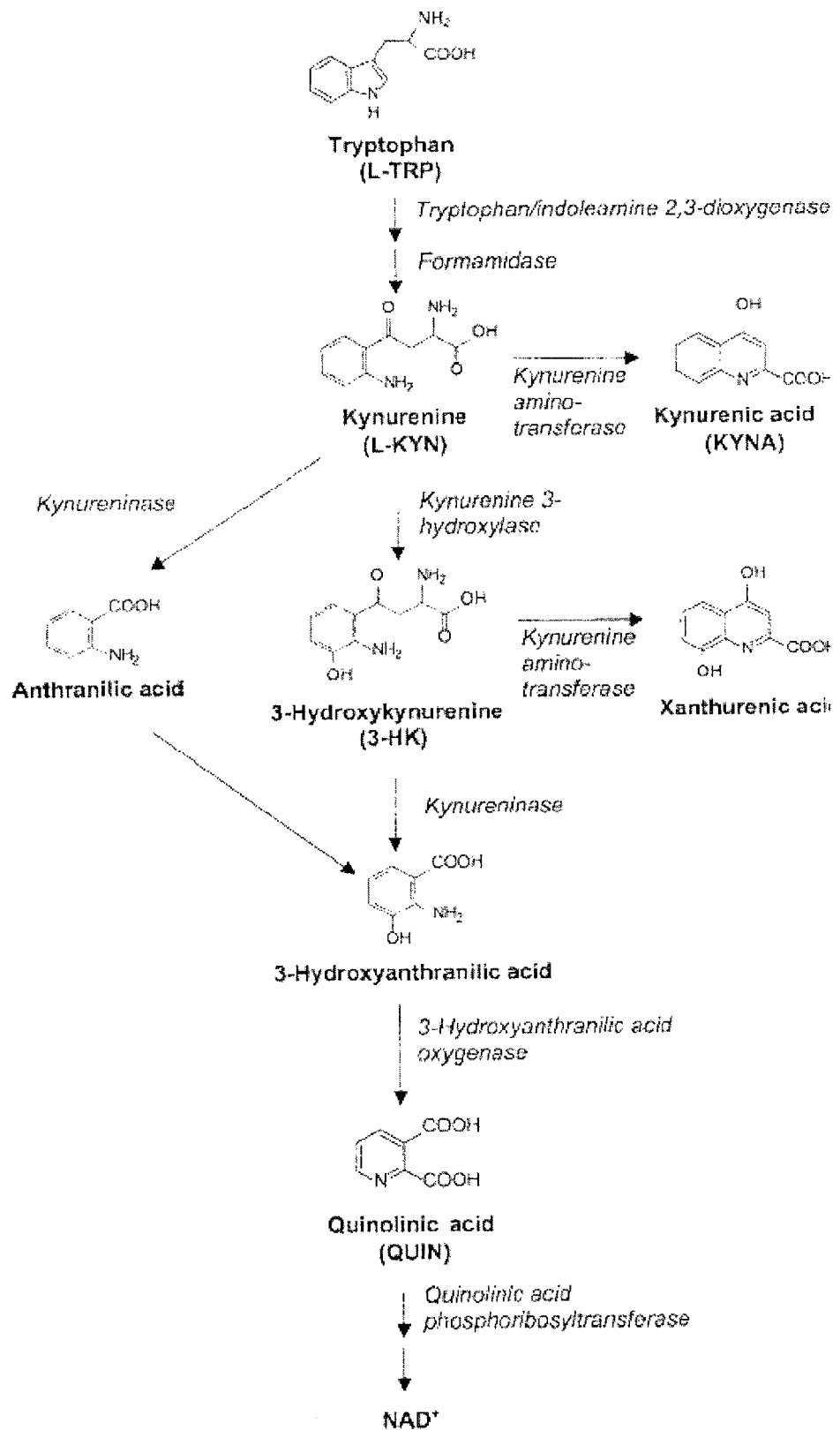
FIG. 1 is a diagram of the kynurenine pathway containing the structures of metabolites and the names of the enzymes that catalyze each step in the pathway.

FIG. 1 is a diagram of the kynurenine pathway containing the structures of metabolites and the names of the enzymes that catalyze each step in the pathway.

Figure 2:
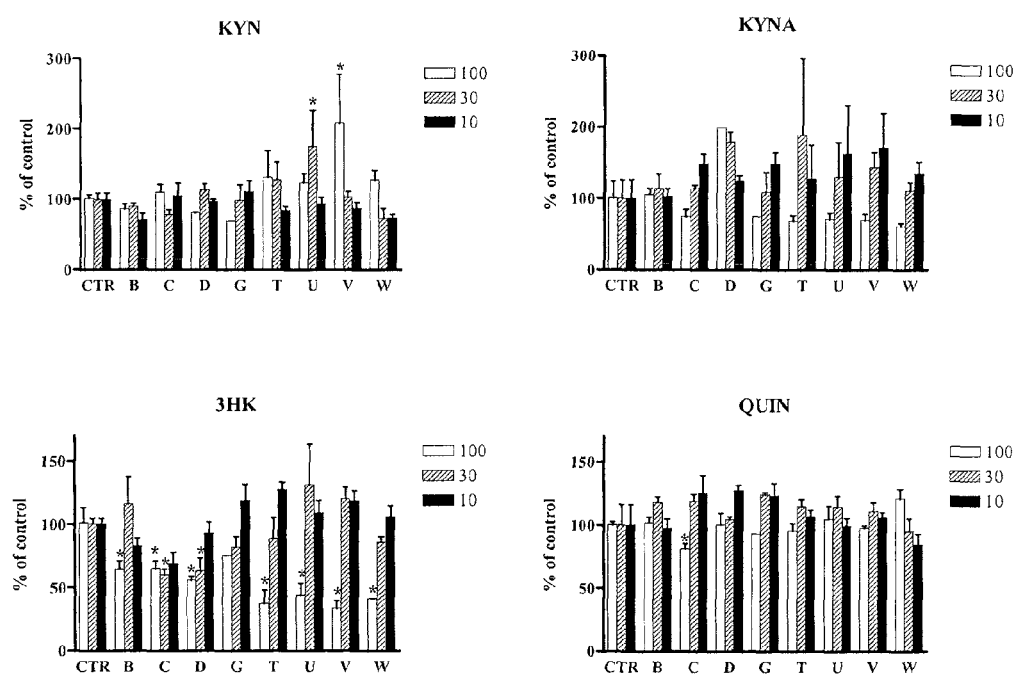
FIG. 2 shows brain kynurenine (KYN) and brain KYN metabolites, kynurenic acid (KYNA), 3-hydroxykynurenine (3HK), and quinolinic acid (QUIN), after different doses of the drugs where the animals were euthanized after 5 h.

FIG. 2 shows brain kynurenine (KYN) and brain KYN metabolites, kynurenic acid (KYNA), 3-hydroxykynurenine (3HK), and quinolinic acid (QUIN), after different doses of the drugs where the animals were euthanized after 5 h.

Figure 3:
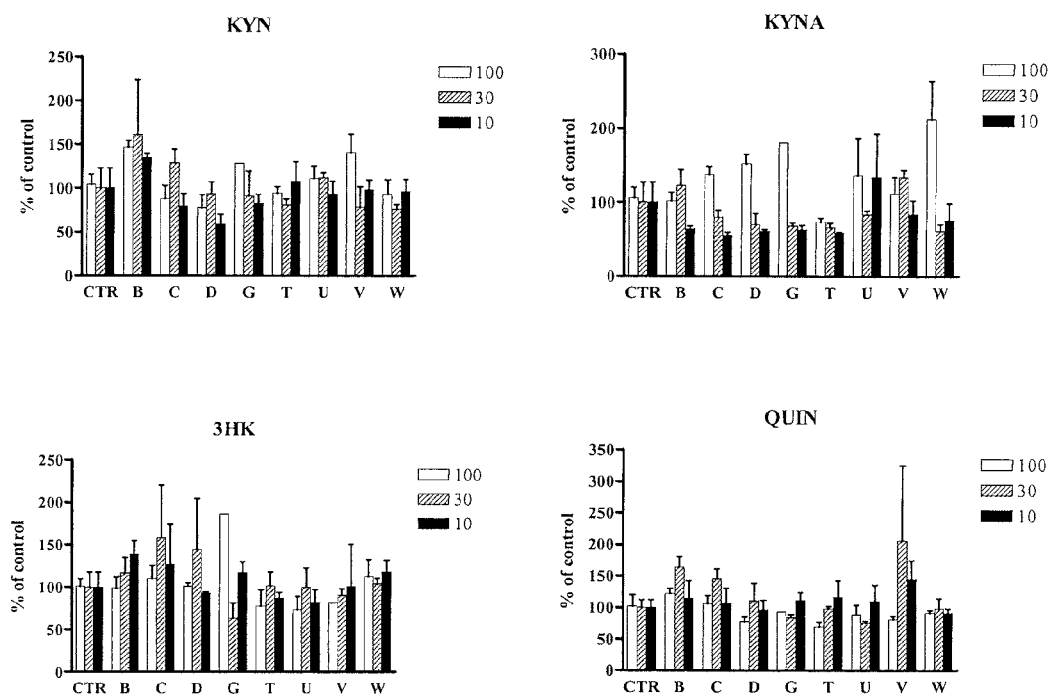
FIG. 3 shows plasma KYN and plasma KYN metabolites, KYNA, 3HK, and QUIN, after different doses of the drugs where the animals were euthanized after 5 h.

FIG. 3 shows plasma KYN and plasma KYN metabolites, KYNA, 3HK, and QUIN, after different doses of the drugs where the animals were euthanized after 5 h.

Figure 4:
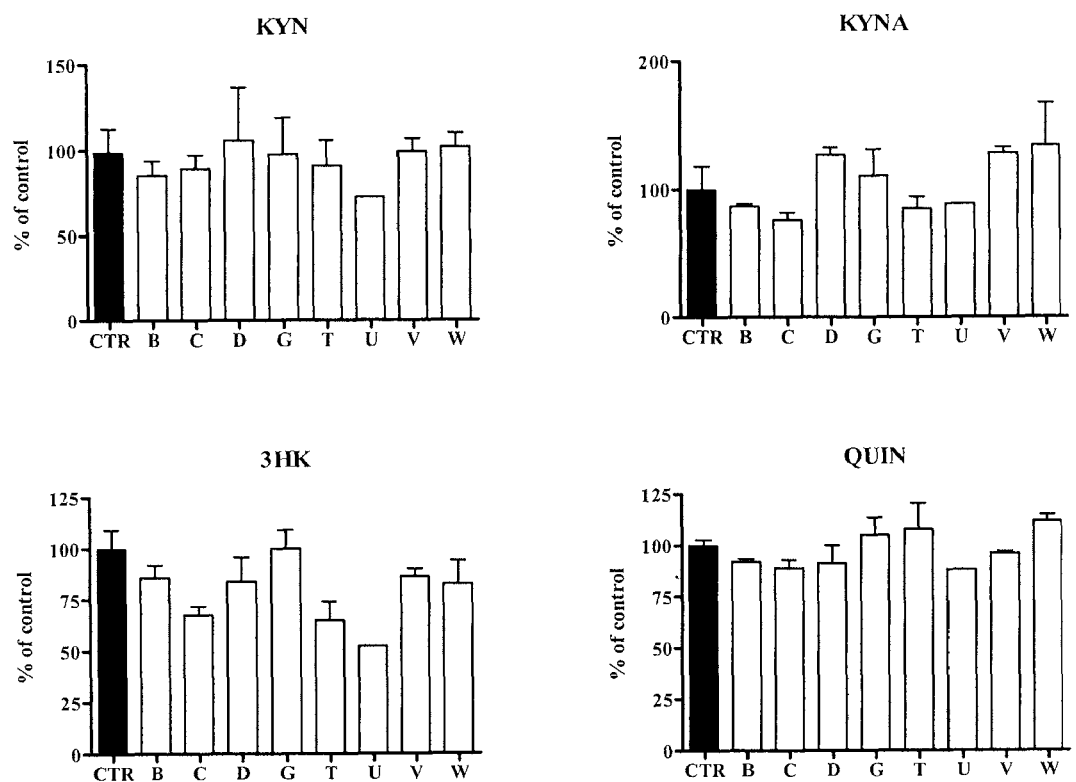
FIG. 4 shows a comparison of the brain KYN and brain KYN metabolites, KYNA, 3HK, and QUIN, after 100 mg/kg dose of the drugs where the animals were euthanized after 10 h.

FIG. 4 shows a comparison of the brain KYN and brain KYN metabolites, KYNA, 3HK, and QUIN, after 100 mg/kg dose of the drugs where the animals were euthanized after 10 h.

Figure 5:
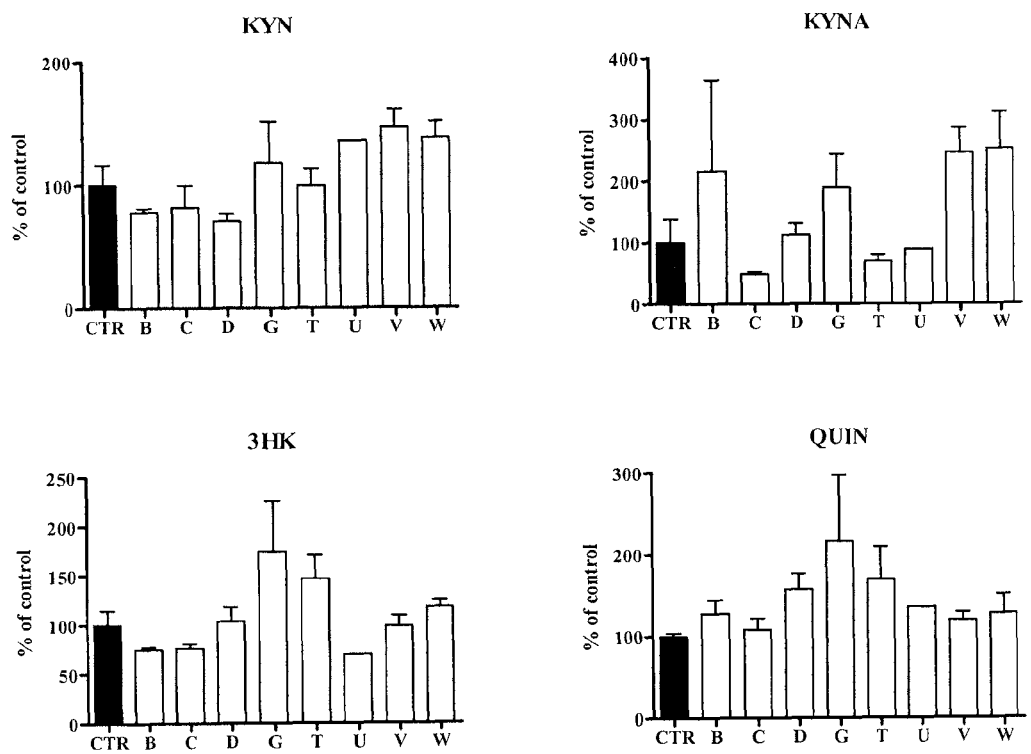
FIG. 5 shows a comparison of the plasma KYN and plasma KYN metabolites, KYNA, 3HK, and QUIN, after 100 mg/kg dose of the drugs where the animals were euthanized after 10 h.

FIG. 5 shows a comparison of the plasma KYN and plasma KYN metabolites, KYNA, 3HK, and QUIN, after 100 mg/kg dose of the drugs where the animals were euthanized after 10 h.

Figure 6:
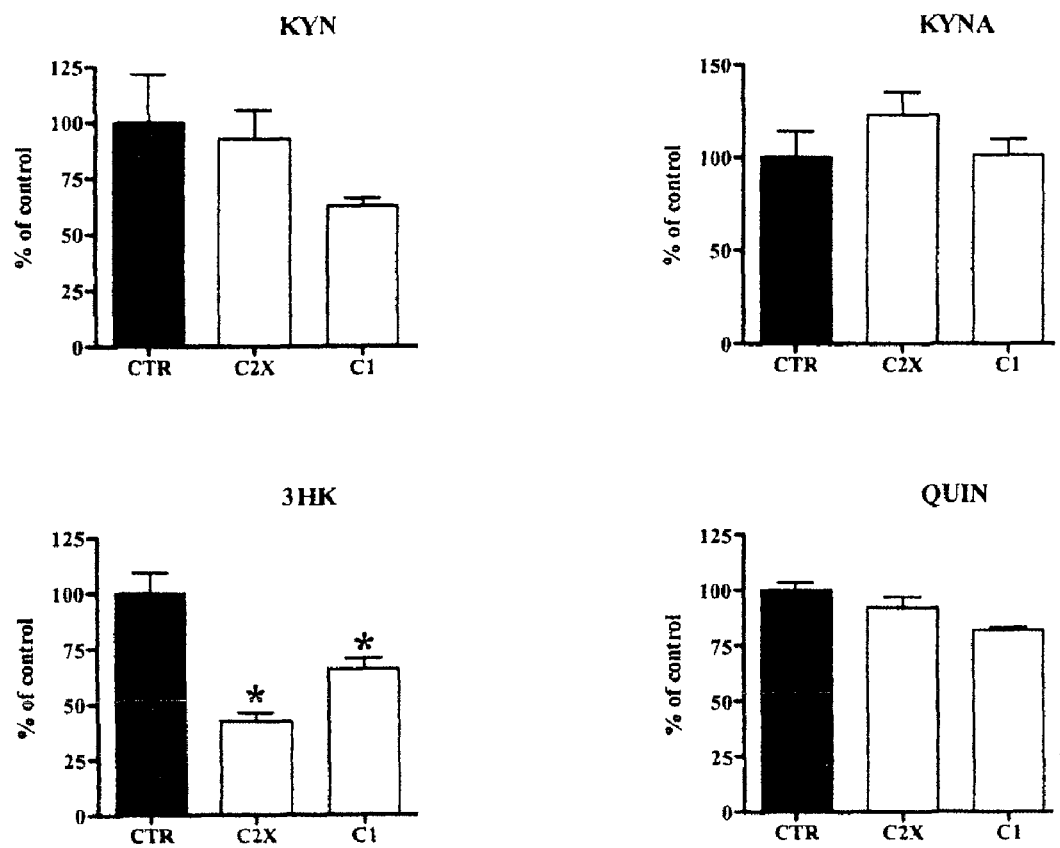
FIG. 6 shows a comparison of the brain KYN metabolites after 100 mg/kg of the drugs where the animals were euthanized 10 h after the administration of compound C twice (at time 0 and at time 5 hours; C2X in the figure) and 5 h after the administration of compound C (C1 in the figure).

FIG. 6 shows a comparison of the brain KYN metabolites after 100 mg/kg of the drugs where the animals were euthanized 10 h after the administration of compound C twice (at time 0 and at time 5 hours; C2X in the figure) and 5 h after the administration of compound C (C1 in the figure).

Figure 7:
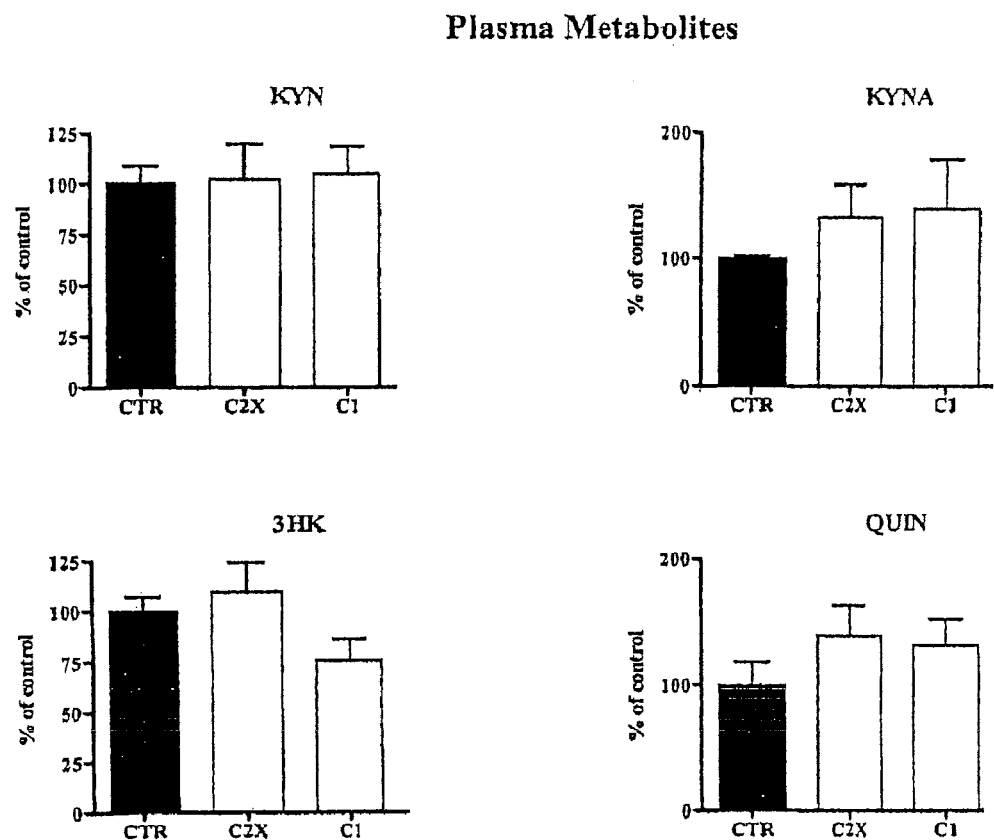
FIG. 7 shows a comparison of the plasma KYN metabolites after 100 mg/kg of the drugs where the animals were euthanized 10 h after the administration of compound C twice (at time 0 and at time 5 hours; C2X in the figure) and 5 h after the administration of compound C (C1 in the figure).

FIG. 7 shows a comparison of the plasma KYN metabolites after 100 mg/kg of the drugs where the animals were euthanized 10 h after the administration of compound C twice (at time 0 and at time 5 hours; C2X in the figure) and 5 h after the administration of compound C (C1 in the figure).

Figure 8:
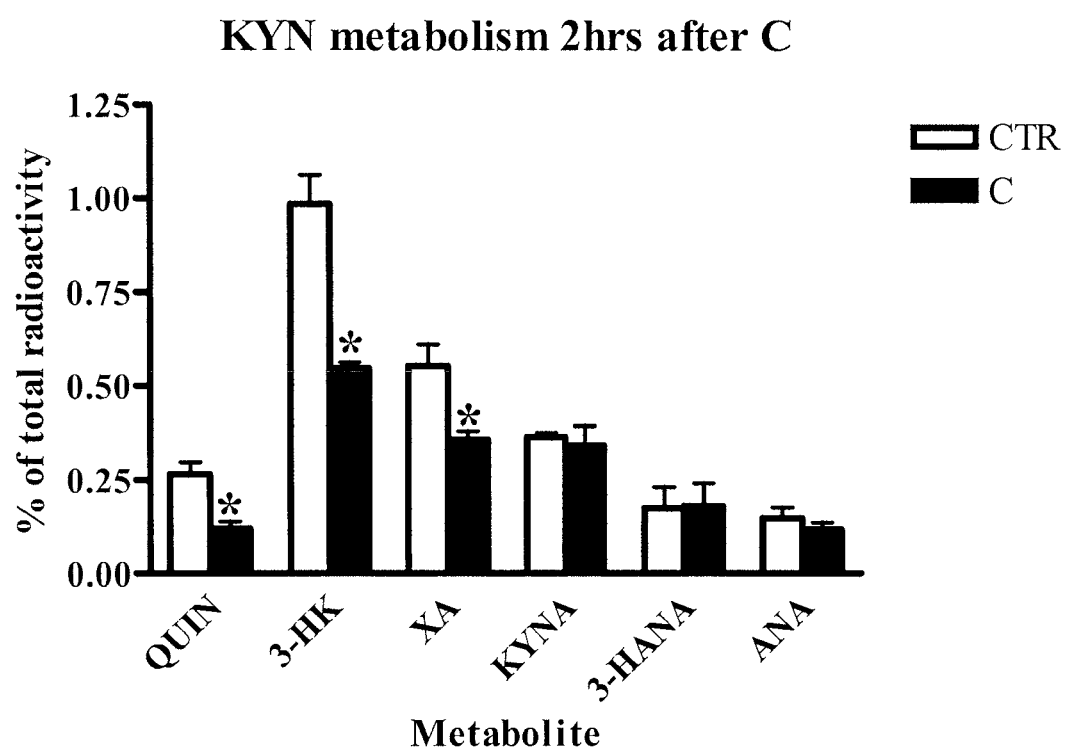
FIG. 8 shows a comparison of the $^3$H-KYN metabolism after treatment with 100 mg/kg of A10. Animals were treated and 2 h after were injected in the striatum with $^3$H-KYN and euthanized 2 h after.

FIG. 8 shows a comparison of the $^3$H-KYN metabolism after treatment with 100 mg/kg of A10. Animals were treated and 2 h after were injected in the striatum with $^3$H-KYN and euthanized 2 h after.

Figure 9:
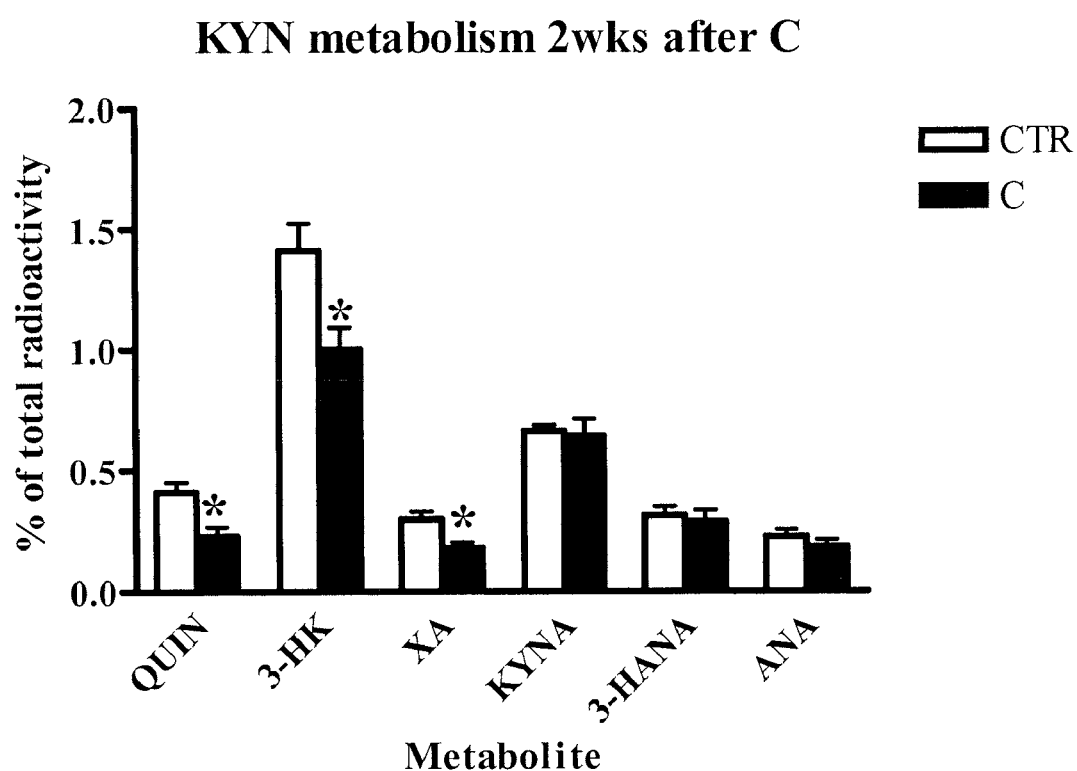
FIG. 9 shows a comparison of the $^3$H-KYN metabolism after treatment with 100 mg/kg/day of A10. Animals were treated for 2 weeks and were injected in the striatum with $^3$H-KYN and euthanized 2 h after.

FIG. 9 shows a comparison of the $^3$H-KYN metabolism after treatment with 100 mg/kg/day of A10. Animals were treated for 2 weeks and were injected in the striatum with $^3$H-KYN and euthanized 2 h after.

Figure 10:
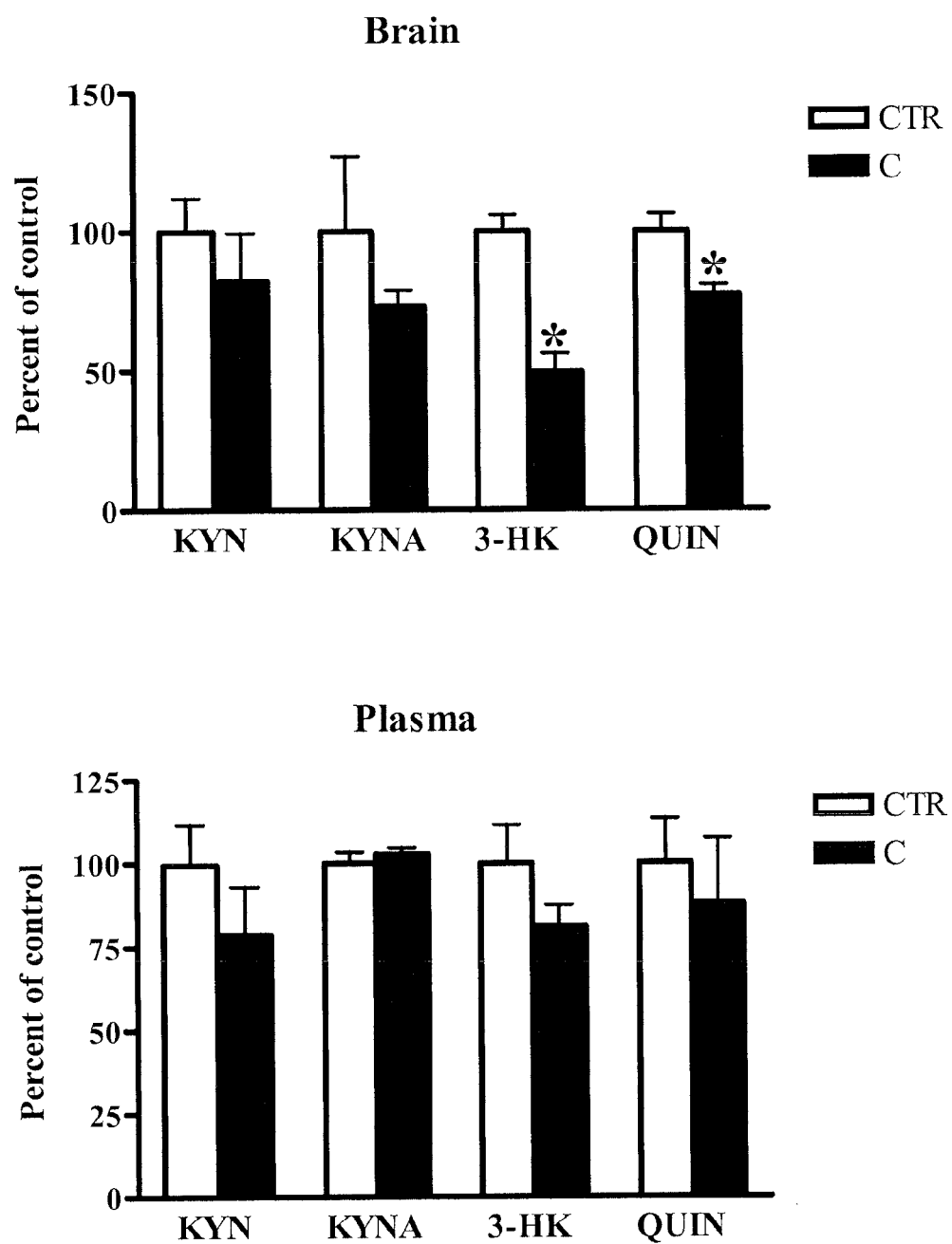
FIG. 10 shows a comparison of the brain and plasma KYN metabolites after 100 mg/kg/day of A10 for 2 days.

FIG. 10 shows a comparison of the brain and plasma KYN metabolites after 100 mg/kg/day of A10 for 2 days.

Figure 11:
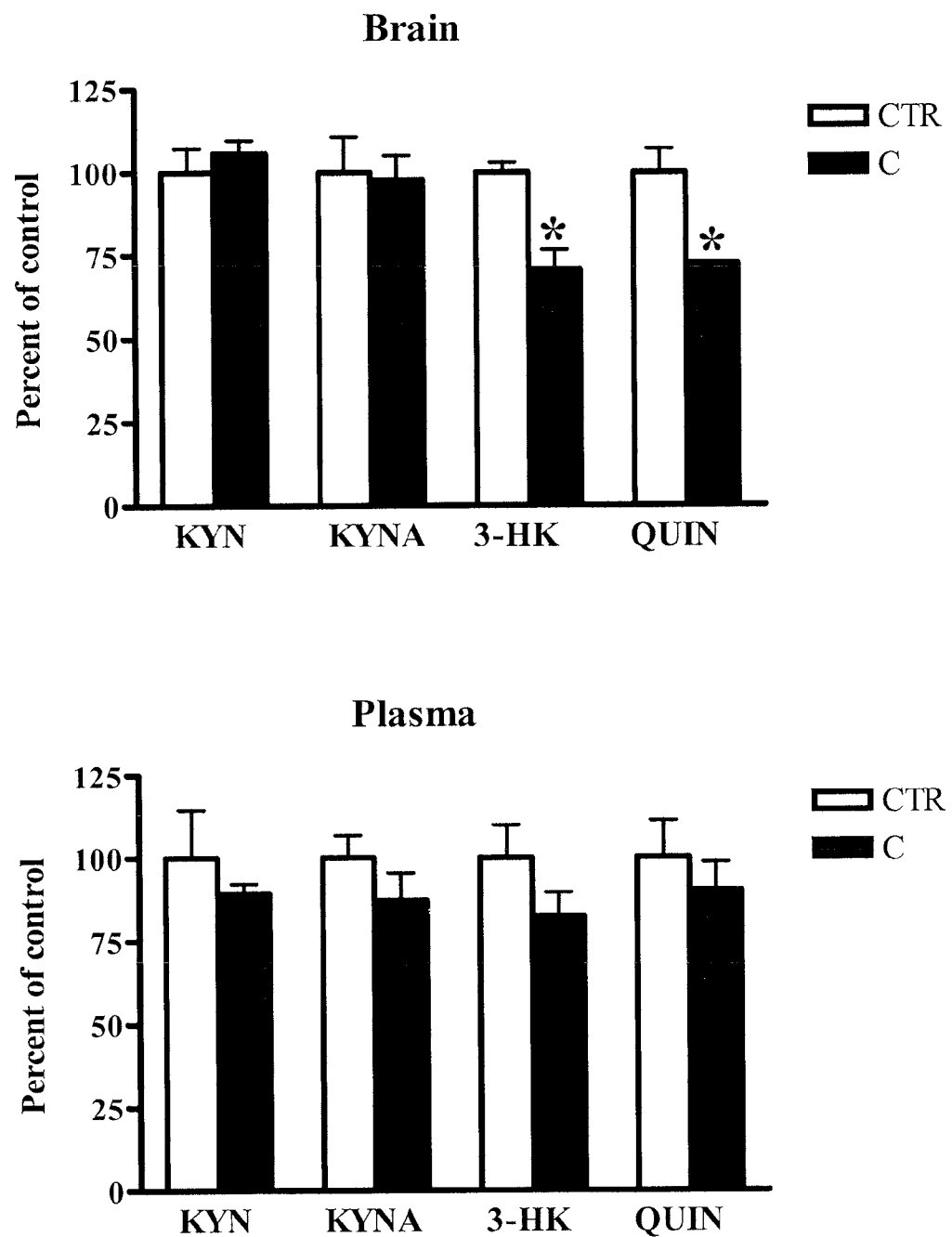
FIG. 11 shows a comparison of the brain and plasma KYN metabolites after 100 mg/kg/day of A 10 for 2 weeks.

FIG. 11 shows a comparison of the brain and plasma KYN metabolites after 100 mg/kg/day of A10 for 2 weeks.

The data establishes the specificity of the biological activity in the brain of the treated mammals.

Example 26

Comparison of the Compounds of the Invention In Vivo

Figure 12:
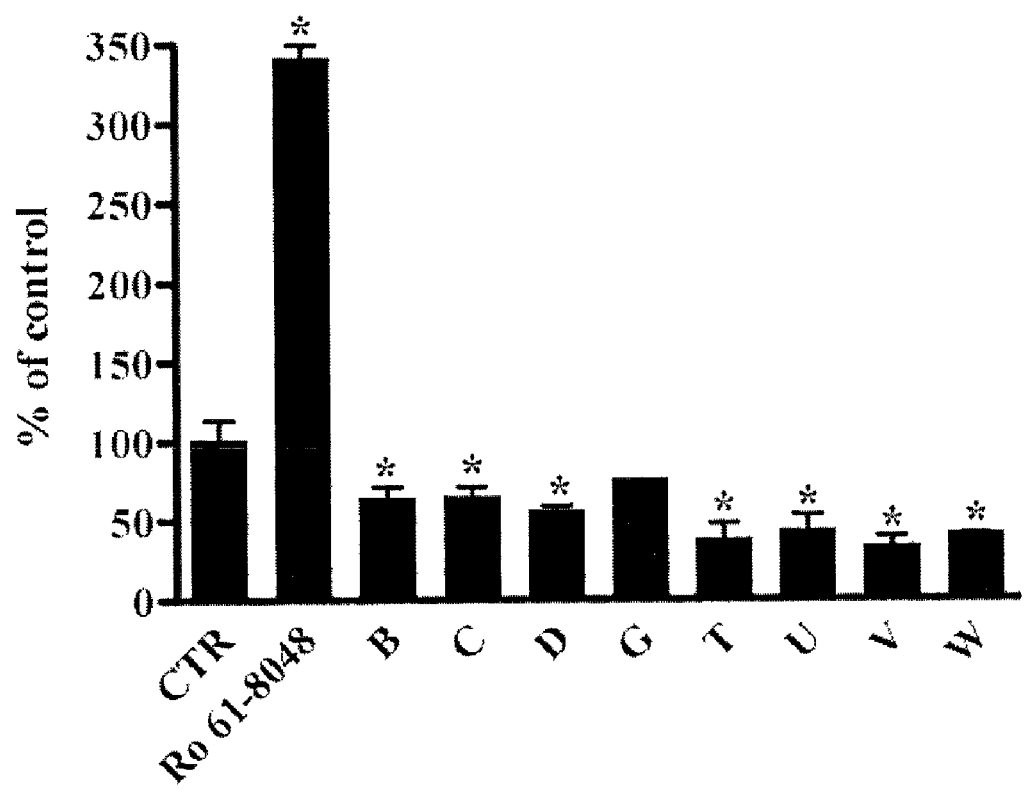
FIG. 12 shows an in vivo data on the comparison of the compound 61-8048 described in U.S. Pat. No. 5,877,193 with the compounds of the invention. The structure of the compound 61-8048 is as below.

FIG. 12 shows an in vivo data on the comparison of the compound 61-8048 described in U.S. Pat. No. 5,877,193 with the compounds of the invention where the data shows that the compound 61-8048 does not decrease 3-HK in the brain after oral administration while the compounds of the invention do. The structure of the compound 61-8048 is as below:

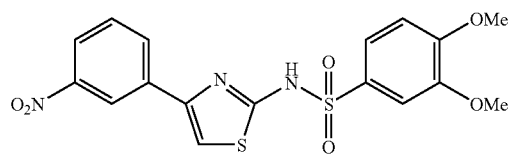

Example 27

Effect of the Compound M (JM6 in FIG. 13) on Survival in a Mouse Model of Huntington's Disease FIG. 13 shows the effect of compound M (JM6 in FIG. 13) on survival in a mouse model of Huntington's disease (the R6/2 model of Huntington's disease [Mangiarini, L. et al. "Exon 1 of the HD gene with an expanded CAG repeat is sufficient to cause a progressive neurological phenotype in transgenic mice" Cell 87, 493-506 (1996)]). The magnitude of the effect of protection of this compound is equal to or greater to that reported for any single agent administered in this model, and also that the compound (61-8048) at 100 mg/kg/day did not have a significant effect on survival (not shown in the figure). The structure of the compound M is

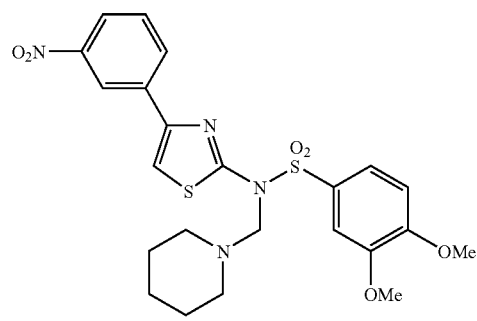

From the foregoing it will be appreciated that, although specific embodiments of the invention have been described herein for purposes of illustration, various modifications may be made without deviating from the spirit and scope of the invention.

What is claimed is:

1. A compound of Formula Ia or Ib:

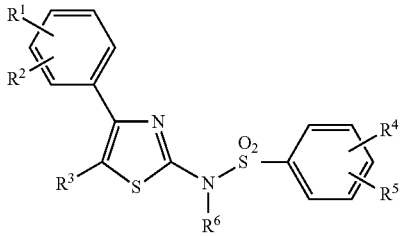

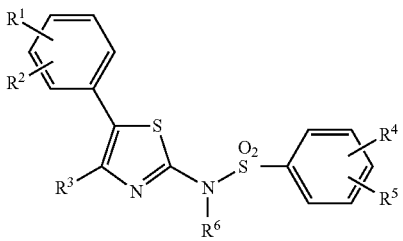

wherein:

$R^1$ and $R^2$ independently are selected from the group consisting of hydrogen, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, wherein at least one of $R^1$ and $R^2$ is selected from the group consisting of nitro, trifluoromethyl, halo, and cyano;

$R^3$ is substituted alky;

$R^4$ and $R^5$ independently are selected from the group consisting of hydrogen, alkyl, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, substituted sulfonyloxy, substituted sulfinyl, and aminocarbonyl, wherein at least one of $R^4$ and $R^5$ is alkoxy; and $R^6$ is selected from the group consisting of hydrogen, alkyl, and substituted alkyl;

or a tautomer and/or a pharmaceutically acceptable salt thereof.

2. A compound according to claim 1, wherein $R^1$ and $R^2$ independently are hydrogen or nitro.

3. A compound according to claim 1, wherein $R^4$ and $R^5$ independently are hydrogen or alkoxy.

4. A compound according to claim 1, wherein $R^3$ is alkyl substituted with 1 to 2 substituents selected from hydroxyl, amino and substituted amino.

5. A compound according to claim 1, wherein $R^6$ is hydrogen.

6. A compound wherein the compound is of Formula II:

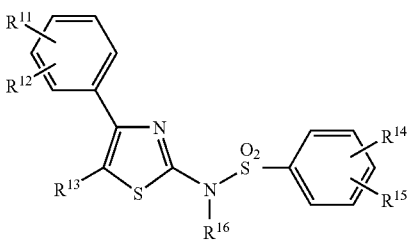

wherein:

$R^{11}$ and $R^{12}$ independently are selected from the group consisting of hydrogen, substituted alkyl, alkoxy, substituted alkoxy, alkenyl, substituted alkenyl, alkynyl, substituted alkynyl, amino, substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, wherein at least one of $R^{11}$ and $R^{12}$ is nitro, trifluoromethyl, halo, or cyano;

$R^{13}$ is substituted alkyl;

$R^{14}$ and $R^{15}$ independently are selected from the group consisting of hydrogen, alkyl, substituted alkyl, alkoxy, substituted alkoxy, alkenyl, substituted alkenyl, alkynyl, substituted alkynyl, amino substituted amino, aminosulfonyl, aminosulfonyloxy, aminosulfonylamino, amidino, carboxyl, carboxyl ester, cyano, halo, hydroxyl, acyl, nitro, mercapto, alkylthio, substituted alkylthio, substituted sulfonyl, sulfonyloxy, substituted sulfinyl, and aminocarbonyl, wherein at least one of $R^{14}$ and $R^{15}$ is alkoxy; and $R^{16}$ is selected from the group consisting of hydrogen, alkyl, and substituted alkyl;

or a tautomer and/or a pharmaceutically acceptable salt thereof.

7. A compound according to claim 6, wherein at least one of $R^{11}$ and $R^{12}$ is nitro, trifluoromethyl, or cyano.

8. A compound according to claim 7, wherein at least one of $R^{11}$ and $R^{12}$ is nitro.

9. A compound according to claim 6, wherein at least one of $R^{14}$ and $R^{15}$ is methoxy.

10. A compound according to claim 6, wherein $R^{13}$ is alkyl substituted with 1 to 2 substituents selected from hydroxyl, amino and substituted amino.

11. A compound according to claim 10, wherein $R^{13}$ is selected from the group consisting of hydroxymethyl, dimethylaminomethyl, pyrrolidin-1-ylmethyl, piperidin-1-ylmethyl, morpholinomethyl, (4-methylpiperazin-1-yl)methyl, (diethylamino)methyl, (methylpropylamino)methyl, thiomorpholinomethyl, and bis(hydroxyethyl)amino)methyl.

12. A compound according to claim 6, wherein $R^{16}$ is hydrogen.

13. A compound according to claim 6, wherein $R^{16}$ is selected from the group consisting of hydrogen, methyl, (ethylcarboxylate)methyl, ethylcarboxylate, and methylcarboxylate.

14. A compound selected from the group consisting of
3,4-dimethoxy-N-[4-(3-nitrophenyl)-5-dimethylaminomethyl-1,3-thiazole-2-yl]benzenesulfonamide;
3,4-dimethoxy-N-[4-(3-nitrophenyl)-5-(pyrrolidin-1-ylmethyl)-1,3-thiazole-2-yl]benzenesulfonamide;

3,4-dimethoxy-N-[4-(3-nitrophenyl)-5-(piperidin-1-ylmethyl)-1,3-thiazole-2-yl]benzenesulfonamide;

3,4-dimethoxy-N-[4-(3-nitrophenyl)-5-morpholinomethyl-1,3-thiazole-2-yl]benzenesulfonamide;

3,4-dimethoxy-N-[4-(3-nitrophenyl)-5-((4-methylpiperazin-1-yl)methyl)-1,3-thiazole-2-yl]benzenesulfonamide;

3,4-dimethoxy-N-[4-(3-nitrophenyl)-5-(diethylamino)methyl-1,3-thiazole-2-yl]benzenesulfonamide;

3,4-dimethoxy-N-[4-(3-nitrophenyl)-5-(methylpropylamino)methyl-1,3-thiazole-2-yl]benzenesulfonamide;

3,4-dimethoxy-N-[4-(3-nitrophenyl)-5-thiomorpholinomethyl-1,3-thiazole-2-yl]benzenesulfonamide;

3,4-dimethoxy-N-[4-(3-nitrophenyl)-5-(bis(hydroxyethyl)amino)methyl-1,3-thiazole-2-yl]benzenesulfonamide; and 3,4-dimethoxy-N-[4-(3-nitrophenyl)-5-(hydroxymethyl)-1,3-thiazole-2-yl]benzenesulfonamide;

or their tautomers and/or a pharmaceutically acceptable salt thereof.

15. A pharmaceutical composition comprising one or more compounds of claim 1 and a pharmaceutically acceptable excipient.

16. A compound of the formula:

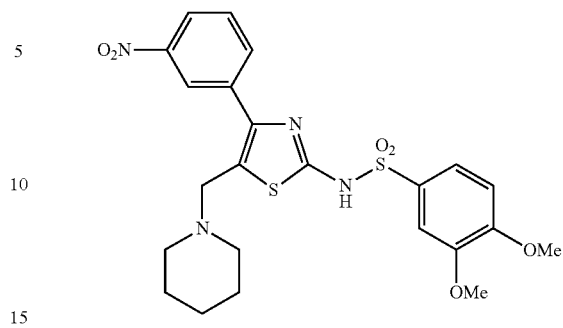

or a tautomer and/or a pharmaceutically acceptable salt thereof.

17. A pharmaceutical composition comprising the compound of claim 16 and a pharmaceutically acceptable excipient.

18. A pharmaceutical composition comprising one or more compounds of claim 6 and a pharmaceutically acceptable excipient.

* * * * *

UNITED STATES PATENT AND TRADEMARK OFFICE
CERTIFICATE OF CORRECTION

PATENT NO. : 7,994,338 B2
APPLICATION NO. : 11/840138
DATED : August 9, 2011
INVENTOR(S) : Paul J. Muchowski et al.

Page 1 of 2

It is certified that error appears in the above-identified patent and that said Letters Patent is hereby corrected as shown below:

IN THE ABSTRACT:

Title Page, Item (57) Structure Ib, please replace " 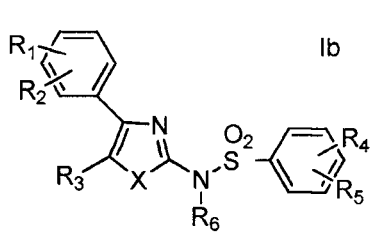 " with -- 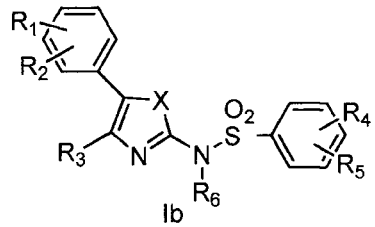 --.

IN THE SPECIFICATION:

Column 3, lines 21-31, please replace " 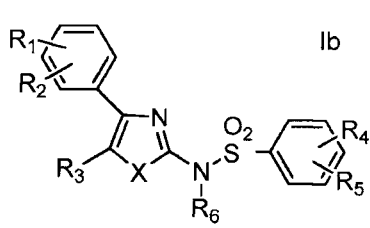 " with -- 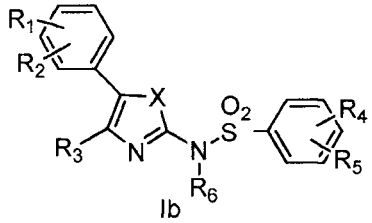 --.

Column 4, lines 29-38, please replace " 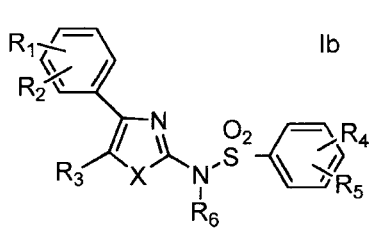 " with -- 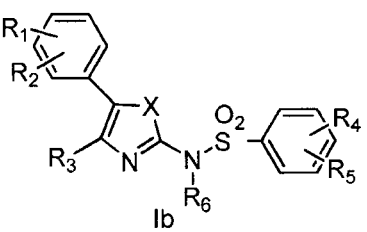 --.

Signed and Sealed this
Fourth Day of October, 2011

David J. Kappos
*Director of the United States Patent and Trademark Office*

Column 16, lines 15-23, please replace " 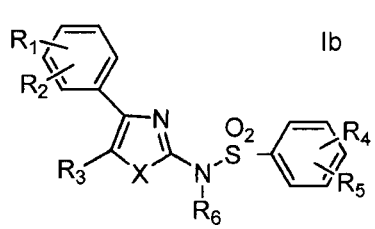 " with -- 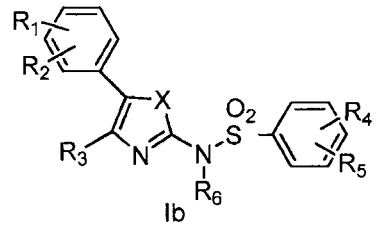 --.

Column 19, line 58, please replace "$R^{16}$ selected from the group consisting of hydrogen" with -- $R^{16}$ is selected from the group consisting of hydrogen --.

Column 33, lines 54-63, please replace " 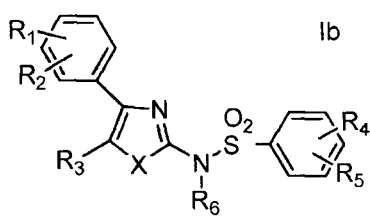 " with -- 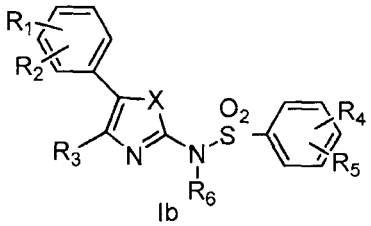 --.

Column 39, line 5, please replace "4-bromobenzenesulfonyl chloride, 2-carboxybenzenesulfon," with -- 4-bromobenzenesulfonyl chloride, 2-carboxybenzenesulfonyl --.

IN THE CLAIMS:

Claim 1, column 61, line 41, please replace "$R^3$ is substituted alky;" with -- $R^3$ is substituted alkyl; --.

Claim 6, column 62, line 31, please replace "substituted alkynyl, amino substituted amino, aminosul-" with -- substituted alkynyl, amino, substituted amino, aminosul- --.

Claim 14, column 63, line 21, please replace "or their tautomers and/or a pharmaceutically acceptable" with -- or a tautomer and/or a pharmaceutically acceptable --.